United States Patent
Spillinger et al.

(10) Patent No.: US 12,059,125 B2
(45) Date of Patent: Aug. 13, 2024

(54) SYSTEMS AND METHODS FOR GENERATING AND DISPLAYING A STUDY OF A STREAM OF IN-VIVO IMAGES

(71) Applicant: Given Imaging LTD, Yoqneam (IL)

(72) Inventors: Avishag Spillinger, Kiriat Haim (IL); Dori Peleg, Kiryat Bialik (IL); Orit Elkayam, Givat Ela (IL); Eva Niv, Hadera (IL); Iddo Ambor, Binyamina (IL); Sherry L. Fox, Sugar Hill, GA (US); Ryan S. Sohlden, Lyons, CO (US)

(73) Assignee: GIVEN IMAGING LTD., Yoqneam (IL)

( * ) Notice: Subject to any disclaimer, the term of this patent is extended or adjusted under 35 U.S.C. 154(b) by 639 days.

(21) Appl. No.: 17/286,641

(22) PCT Filed: Oct. 19, 2019

(86) PCT No.: PCT/IL2019/051133
§ 371 (c)(1),
(2) Date: Apr. 19, 2021

(87) PCT Pub. No.: WO2020/079696
PCT Pub. Date: Apr. 23, 2020

(65) Prior Publication Data
US 2021/0345865 A1    Nov. 11, 2021

Related U.S. Application Data

(60) Provisional application No. 62/849,508, filed on May 17, 2019, provisional application No. 62/807,018, (Continued)

(51) Int. Cl.
*A61B 1/00* (2006.01)
*A61B 1/04* (2006.01)
*G06T 7/00* (2017.01)

(52) U.S. Cl.
CPC .... *A61B 1/000094* (2022.02); *A61B 1/00045* (2013.01); *A61B 1/041* (2013.01); (Continued)

(58) Field of Classification Search
CPC .......... A61B 1/000094; A61B 1/00045; A61B 1/041; A61B 1/00016; A61B 1/0005; (Continued)

(56) References Cited

U.S. PATENT DOCUMENTS

| 8,423,123 B2 * | 4/2013 | Horn ........................ A61B 1/04 |
| | | 600/407 |
| 8,792,691 B1 | 7/2014 | Rozenfeld et al. |

(Continued)

FOREIGN PATENT DOCUMENTS

| EP | 2165639 A1 | 3/2010 |
| JP | 2007125373 A | 5/2007 |

(Continued)

OTHER PUBLICATIONS

Szczypiński P, Klepaczko A, Pazurek M, Daniel P. Texture and color based image segmentation and pathology detection in capsule endoscopy videos. Computer methods and programs in biomedicine. Jan. 1, 2014;113(1):396-411. (Year: 2014).*

(Continued)

*Primary Examiner* — Fayyaz Alam
(74) *Attorney, Agent, or Firm* — Carter, DeLuca & Farrell LLP

(57) ABSTRACT

Systems and methods may display and/or provide analysis of a number of selected images of a patients gastrointestinal tract collected in-vivo by a swallowable capsule. Images may be displayed for review (e.g., as a study) and/or for further analysis by a user. A subset of images representing the stream of images and automatically selected according to a first selection method may be displayed. On user input, (Continued)

additional images corresponding to a currently displayed image may be displayed, where the additional images are automatically selected according to a second selection method. The second selection method may be based on a relation between images of the stream of in-vivo images and the currently displayed image.

31 Claims, 13 Drawing Sheets

Related U.S. Application Data filed on Feb. 18, 2019, provisional application No. 62/747,786, filed on Oct. 19, 2018.

(52) U.S. Cl.
CPC .. *G06T 7/0012* (2013.01); *G06T 2207/10016* (2013.01); *G06T 2207/10068* (2013.01)

(58) Field of Classification Search
CPC ............ A61B 1/00055; G06T 7/0012; G06T 2207/10016; G06T 2207/10068; G16H 15/00; G16H 30/40
See application file for complete search history.

(56) References Cited

U.S. PATENT DOCUMENTS

| | | | |
|---|---|---|---|
| 8,900,124 B2* | 12/2014 | Hirakawa | A61B 1/041 600/109 |
| 9,060,673 B2* | 6/2015 | Krupnik | G06F 3/0482 |
| 9,589,374 B1 | 3/2017 | Gao et al. | |
| 2005/0075537 A1 | 4/2005 | Chen et al. | |
| 2005/0196023 A1 | 9/2005 | Chen et al. | |
| 2007/0066875 A1 | 3/2007 | Horn et al. | |
| 2007/0078335 A1* | 4/2007 | Horn | A61B 1/04 600/425 |
| 2007/0167715 A1 | 7/2007 | Shigemori | |
| 2009/0023993 A1 | 1/2009 | Davidson et al. | |
| 2009/0077128 A1* | 3/2009 | Kimoto | A61B 1/00045 |
| 2010/0094104 A1 | 4/2010 | Nagase et al. | |
| 2011/0164126 A1 | 7/2011 | Ambor et al. | |
| 2012/0316421 A1 | 12/2012 | Kumar et al. | |
| 2016/0048637 A1* | 2/2016 | Nishiyama | A61B 1/041 382/305 |
| 2017/0119236 A1 | 5/2017 | Hyde et al. | |
| 2017/0272699 A1 | 9/2017 | Stopek | |

FOREIGN PATENT DOCUMENTS

| | | |
|---|---|---|
| JP | 2007151809 A | 6/2007 |
| JP | 2013075244 A | 4/2013 |
| JP | 6425868 B1 | 11/2018 |
| WO | 2009008125 A1 | 1/2009 |
| WO | 2010082993 A2 | 7/2010 |
| WO | 2012137705 A1 | 10/2012 |
| WO | 2018002935 A1 | 1/2018 |
| WO | 2018105221 A1 | 6/2018 |
| WO | 2018112255 A1 | 6/2018 |
| WO | 2019087971 A1 | 5/2019 |

OTHER PUBLICATIONS

Lakovidis DK, Koulaouzidis A. Automatic lesion detection in capsule endoscopy based on color saliency: closer to an essential adjunct for reviewing software. Gastrointestinal endoscopy. Nov. 1, 2014;80(5):877-83. (Year: 2014).*

Mackiewicz M, Berens J, Fisher M. Wireless capsule endoscopy color video segmentation. IEEE Transactions on Medical Imaging. May 23, 2008;27(12):1769-81. (Year: 2008).*

International Search Report and Written Opinion of the International Searching Authority issued in corresponding application PCT/IL2019/051133 mailed Jan. 23, 2020 (7 pages).

Extended European Search Report issued in corresponding application EP 19873352.9 dated Mar. 22, 2022 (14 pages).

Office Action issued in corresponding Japanese Application No. 2021-521094 mailed Jul. 14, 2023, together with English Language translation (12 pages).

Japanese Office Action for application No. 2021-521094 dated Jan. 5, 2024 with English Translation, 6 pages.

Chinese Office Action for application No. 201980075047.5 dated Mar. 19, 2024 with English translation, 14 pages.

Japanese Office Action for application No. 2021-568563 dated May 29, 2024 with English Translation, 9 pages.

* cited by examiner

FIG. 3

SYSTEMS AND METHODS FOR GENERATING AND DISPLAYING A STUDY OF A STREAM OF IN-VIVO IMAGES

CROSS-REFERENCE TO RELATED APPLICATIONS

This application is a U.S. National Stage Application filed under 35 U.S.C. § 371(a) of International Patent Application No. PCT/IL2019/051133, filed on Oct. 19, 2019, which claims the benefit of the filing date of provisional U.S. Patent Application No. 62/747,786, filed on Oct. 19, 2018, provisional U.S. Patent Application No. 62/807,018, filed on Feb. 18, 2019, and provisional U.S. Patent Application No. 62/849,508, filed on May 17, 2019.

FIELD OF THE INVENTION

The present disclosure relates to methods, systems and computer program products for displaying and/or analyzing and/or reporting medical images from a series or stream of images captured in vivo. In particular, the present disclosure relates to methods, systems and computer program products for generating and displaying a study of in-vivo images captured via a Capsule Endoscopy (CE) procedure.

BACKGROUND

Capsule systems may include a swallowable capsule capturing images of the gastrointestinal tract ("GI" tract or "GIT"). The images may be stored on the capsule and/or transmitted to a receiving device typically including an antenna. The receiving device receives and may store (e.g. within a storage device in the receiving device) the images. The swallowable capsule may include one or more cameras or imaging devices, power source(s), processor(s), and transmitter(s).

The capsule, the receiving device or a removable storage device of the receiving device may be coupled with a computing device, such as a server. The computing device may process the received images and may provide an interface to display the images, typically as a video or movie (e.g. a series of moving images). Such processing may also be performed "locally", on a workstation operated by a medical professional, after accepting images transferred from a receiver or recorder. In some embodiments, a physical receiving device located on a patient may transfer or download images to a computer for processing and viewing. A workstation used to process or view images may be a local computer, tablet or workstation.

A health professional such as a doctor may review the images as they are displayed, e.g., on a workstation, a terminal or remotely, e.g., via a web browser, as the health professional typically views the images as a movie or image stream (which typically includes less images than all captured images due to, for example, pre-processing).

It is desirable to present the thousands of images collected by the capsule in a manner so that the health professional can accurately review the images and spot important images or features and in a reasonable time.

A typical prior art view of a procedure results or of a procedure study seen by a doctor includes thousands of images viewed as a moving image or video (e.g. displaying one image at a time in sequence for each stream of images captured by a single camera). Viewing thousands of images takes valuable time and may be a tiresome task. Viewing thousands of images and as a video, may also lead to a higher probability of missing images of interest. It is desirable to shorten the time a medical professional takes to view images. It is also desired to make the view task more efficient and more beneficial.

BRIEF DESCRIPTION OF THE DRAWINGS

Embodiments of the invention are illustrated by way of example and not limitation in the figures of the accompanying drawings, in which like reference numerals indicate corresponding, analogous or similar elements, and in which:

FIG. 3 shows an example screen, according to some embodiments.

Figure 1:
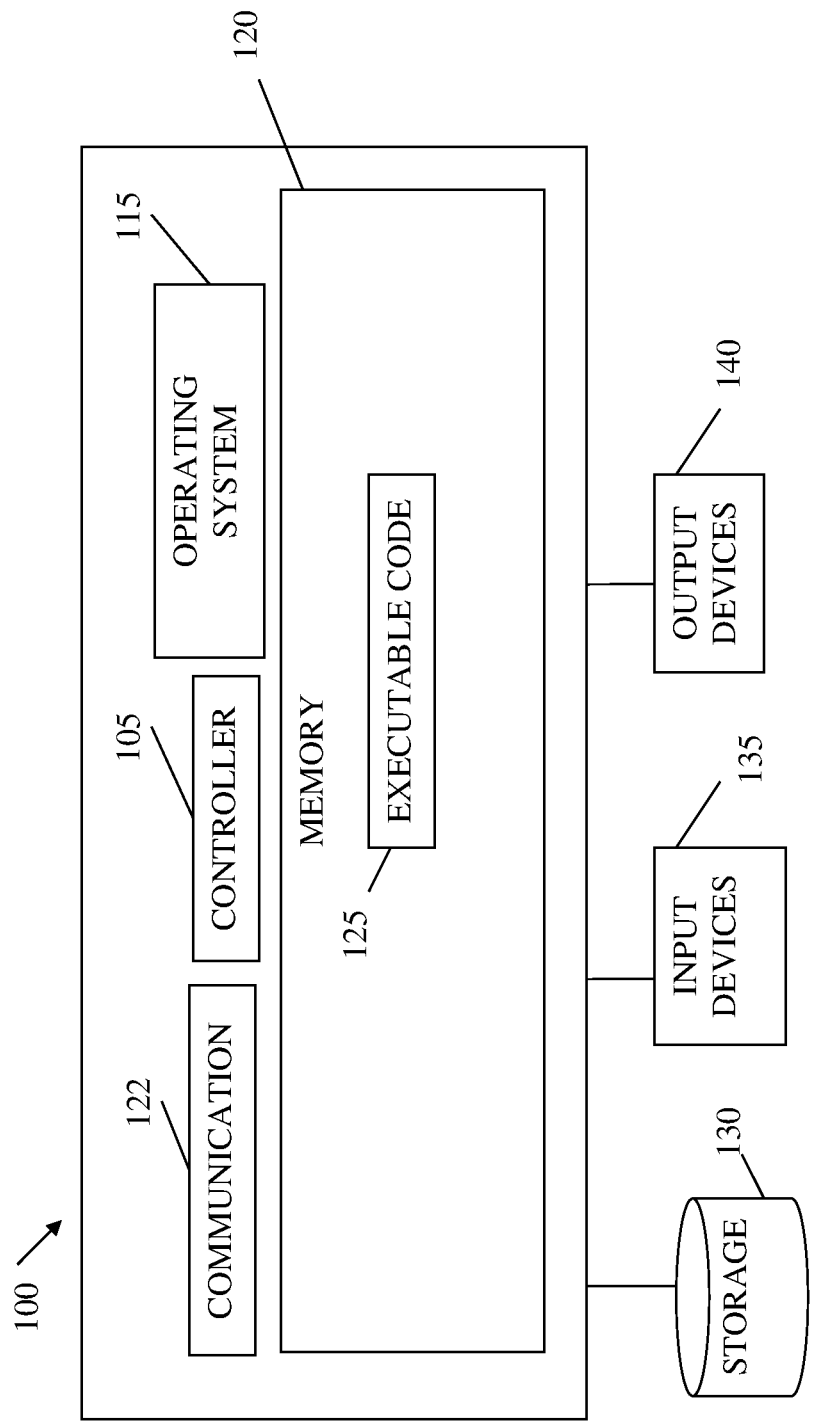
FIG. 1 is a high-level block diagram of an exemplary computing device which may be used with embodiments of the present invention.

It will be appreciated that for simplicity and clarity of illustration, elements shown in the figures have not necessarily been drawn accurately or to scale. For example, dimensions of some of the elements may be exaggerated or more emphasized relative to other elements for clarity, or several physical components may be included in one functional block or element. Further, where considered appropriate, reference numerals may be repeated among the figures to indicate corresponding or analogous elements.

SUMMARY

Embodiments of the present invention may include a capsule device and optionally a receiving device. The capsule device may be a swallowable capsule capturing images while traversing the gastrointestinal tract and transmitting images to the receiving device which typically includes an antenna. The receiving device may receive the images and store them, e.g. within a storage device in the receiving device. The receiving device may transmit the images in real-time (e.g., during a procedure) to a "cloud" based server or another remote device. The receiving device may be, for example, a belt or a patch or any other item worn on a patient. The receiving device may forward the received images to a remote device, for display, including real-time display, storage, processing and/or analysis. The receiving device may transmit the images to a remote device, e.g., via the patient's cellular telephone. A local or remote (e.g. "cloud") server or any other suitable computing device may process and analyze the images and other procedure related data received (e.g., image capture time and patient data) to generate a study of the CE procedure. The computing device may provide an interface, locally or remotely, to display the study for review by a user (e.g., a medical professional). Other methods of storing, receiving, processing and displaying images may be used.

Embodiments of the present invention include systems, methods and computer program products for displaying and/or providing analysis of a number of selected images for review (e.g., a study) and/or for further analysis by a viewer or a user. The images are selected from a stream of images captured in-vivo by a capsule endoscope traversing portions of the gastrointestinal tract, such as the small bowel and/or the colon. The disclosed methods, systems, tools and/or computer program products may be used, inter alia, for diagnosis, making of therapeutic decisions, monitoring, and/or screening of the various pathologies, disorders, anomalies and diseases of the GIT.

Images may be displayed for review (e.g., as a study) and/or for further analysis by a user. A subset of images representing the stream of images and automatically selected according to a first selection method may be displayed. On user input, additional images corresponding to a currently displayed image may be displayed, where the additional images are automatically selected according to a second selection method. The second selection method may be based on a relation between images of the stream of in-vivo images and the currently displayed image.

DETAILED DESCRIPTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention. Some features or elements described with respect to one embodiment may be combined with features or elements described with respect to other embodiments. For the sake of clarity, discussion of same or similar features or elements may not be repeated.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. The term set when used herein may include one or more items. Unless explicitly stated, the method embodiments described herein are not constrained to a particular order or sequence. Additionally, some of the described method embodiments or elements thereof can occur or be performed simultaneously, at the same point in time, or concurrently.

The term "location" and its derivatives, as referred to herein with respect to an image, may refer to the estimated location of the capsule along the GIT while capturing the image or to the estimated location of the portion of the GIT sown in the image along the GIT.

A type of capsule endoscopy procedure may be determined, inter alia, based on the portion of the GIT that is of interest and is to be imaged (e.g., the colon or the small bowel ("SB")), or based on the specific use (e.g., for checking the status of a GI disease, such as Crohn's disease, or for colon cancer screening).

The terms screen/s, view/s and display/s may be used herein interchangeably and may be understood according to the specific context.

The terms "default view", "default display" and "default screen", as referred to herein, may correspondingly refer to a "view", "display" and "screen" which is first displayed upon each initiation of a review of a study of a procedure according to the present systems and methods, and wherein this first view, display or screen is predefined and is not a result of user selection.

The terms "default view" and "default display", as referred to herein with respect to a view or display of specific information, may correspondingly refer to a first "view" and "display" of the specific information upon each initiation of a review of a study of a procedure according to the present systems and methods, and wherein this first view or display of the specific information is predefined and is not a result of user selection.

The terms "by default" or "as default", as referred to herein with respect to a display or view of specific information, may relate to information which is displayed in the frame of a specific view, display or screen with no need for a user action or input to upload, initiate or trigger the display.

The terms "surrounding" or "adjacent" as referred to herein with respect to images (e.g., images which surround another image/s, or which are adjacent to other image/s), may relate to spatial and/or temporal characteristics unless specifically indicated otherwise. For example, images which surround or are adjacent to other image/s may be images which are estimated to be located near the other image/s along the GIT and/or images which were captured near the capture time of another image, within a certain threshold, e.g. within one or two centimeters, or within one, five, or ten seconds.

The terms "GIT" and "a portion of the GIT" may each refer to or include the other, according to their context. Thus, the term "a portion of the GIT" may also refer to the entire GIT and the term "GIT" may also refer only to a portion of the GIT.

Embodiments of the present invention may differ from prior art CE procedure viewing applications in that prior art applications typically present, as a first or default view or display, a movie or image stream—e.g. a series of images presented as a series in time. In embodiments of the present invention, a set of images collected from a GIT via e.g. a swallowable capsule may be processed and then initially presented, e.g. as a default or first view, as a set of still images, e.g. once the images are uploaded or processed, after being captured by a capsule and upon each initiation of a review of a study of a procedure according to the embodiments of the described systems and methods. Each image presented in a default view may be of a feature of interest (e.g. a specific instance of a pathology) and may be associated with or corresponding to other images of that same feature (e.g. of that same instance of pathology) which are not shown in the default view. Indicating or selecting (e.g. clicking on using an input device) the single still image displayed to represent the instance of the feature of interest may present a second level or additional information view, which may be for example a moving image or scrollable series of images which also show that instance of the feature.

Images of different portions of the GIT (e.g. SB), large intestine or colon, esophagus, stomach, etc.) may be presented, and the user interface may vary according to the different portions displayed. The type of procedure performed, e.g., an SB procedure or a colon procedure or a procedure of both (e.g., a procedure aimed to specifically exhibit or check the SB or a procedure aimed to specifically exhibit or check the colon or both), may determine which portion of the GIT is the portion of interest. Typically, most images displayed are of the portion of interest. Each portion of interest may be divided into segments. Each segment (e.g., images showing portions of the GIT estimated to be located in that segment) may be displayed in a different view, e.g., via a different tab. For example, if the portion of interest is colon (e.g., the procedure is a colon procedure), it may be segmented into five anatomical segments (cecum, ascending, transverse, descending, and rectum), each segment having a separate view accessible via a tab. Accordingly, a user may be presented with tabs labeled cecum, ascending, transverse, descending, and rectum, and clicking on cecum may show a set of first-level estimated to best represent the images of the received stream of images estimated to be located in the cecum.

Second level images may be displayed on the same screen as first level images (e.g. a first level image may transition to be displayed as a moving image or a scrollable image to display its corresponding second level images, with other first level still images remaining on a display), or in a different window or popup window. Images of the second level may precede and/or follow or succeed the corresponding first level image according to image capture time. The second level images may include the corresponding first level image (the seed image) or the display of the second level images may include the corresponding first level image. Accordingly, the second level images including or with the addition of the corresponding first level image may be displayed according to their capture time. The second level images may be then numbered such that the first level image (e.g., the "best" representative image), being numbered zero, and the second level images or other second level images being numbered by their distance in images from image zero.

A user may click on a checkbox or otherwise select an image displayed in a first level to have that image placed in a report or final report (typically displayed or delivered after a user reviews the images); a user may filter on images in a first level to cause display of only "selected" images. Various tools or image analysis capabilities may be presented, such as an automatic pathology size estimation and a pathology size estimation tool (e.g., for polyps). Images may be filtered and/or selectively displayed based on user input in other manners.

Different types of image displays or views may be selected by a user, such as a matrix or grid view, a carousel view (e.g., where images are displayed as if seen edge-on of a ring of images, with one "current" image being largest at the front and other images in decreasing size around the "ring"). A map or "heat map" may relate certain images to their spatial orientation along the GIT, with certain features or combinations of features having a "spread" or length of the feature indicated along the heat map, e.g. using color. The map may represent a portion of the GIT, or a portion of interest of the GIT. The map may correspond to the first level images, in that the map may represent a portion of the GIT in which the images were taken, and/or include markers corresponding to the estimated location of the images. A map may thus include localized image indications or markers representing the images according to their location or estimated location in the GIT.

When used herein, processor derived descriptions such as a location, size or cleansing level may be estimated or approximated, based on information available to a processor and the algorithmic method.

A user may add information to an image, and/or information may be automatically added to an image. For instance, a user may label an image using selectable pathology types. A process may automatically draw a box or border around a location of a pathology automatically identified in an image within the image.

According to some aspects, creation or generating of the study may include generating additional information or second level information, in addition to the additional one or more images corresponding to images of the subset of images. For example, the additional information may include division of at least the portion of interest of the GIT into segments, locations of images of the stream of images along at least the portion of interest of the GIT, a map representing at least the portion of interest of the GIT including indications of images of the subset of images along at least the portion of interest of the GIT, a predefined number of images selected from the subset of images according to a third selection method, indications of features of interest in images, indication of cleansing level determined per image, segments and/or per procedure, indication of estimated size of a feature of interest, indication of extent of a feature of interest, a selection of images of the stream of in-vivo images representing transition between anatomical sections of at least the portion of interest of the GIT, and a combination thereof.

In some aspects, a system or method may display a study of a capsule endoscopy procedure, including images captured by a capsule (e.g. swallowed by a patient) during the capsule endoscopy procedure for a user's review. A system may receive a subset of images (e.g., a first level images) selected from a stream or set of in-vivo images of at least a portion of the patient's or subject's GIT captured via the capsule endoscopy procedure. According to some aspects, the system may receive the stream or set of in-vivo images of at least a portion of the patient's or subject's GIT. The system may then automatically choose or select the subset of images from the received stream or set of in-vivo images according to a first selection method, the subset of images "representing" the received stream or set of in-vivo images. By "representing", it is meant, representing from the aspect of or for the benefit of making a medical diagnosis and for making therapeutic decisions with respect to the portion of interest of the patient's GIT. For example, a system may identify one or more features of interest (e.g. one or more types of pathologies) in the received images. The one or more features of interest may be predetermined based on the specific type of capsule endoscopy procedure. Based on that identification of features of interest, the subset of images may be selected to, inter alia, represent the identified pathologies.

For each image of at least a portion of the subset of images, the system may receive, choose or identify one or more images from the stream or set of in-vivo images, which corresponds to the image of the subset of images (e.g., a second level images). The one or more corresponding images may be selected according to a second selection method. According to some aspects, for each image of the subset of images, a corresponding one or more images are selected and received. According to some aspects, the selected corresponding one or more images may include the corresponding image of the subset of images. According to some aspects, the corresponding one or more images may not include images of the subset of images. According to some aspects, the system may select the corresponding one or more images according to a second selection method.

The second selection method may be based on a filter or relation between images of the stream of in-vivo images. Such a filter or relation between images may be, images identified to include at least a portion from the same feature (e.g., the same specific ulcer) or the same type of feature (e.g., images identified to include ulcers), images which were captured in time proximity along the GIT or images which are located adjacently along the GIT, or a combination thereof. According to some aspects, a predefined number of images selected from the subset of images may be received and displayed. The predefined number of images (e.g., five images, ten images, or any number up ten) may be displayed upon receipt of user input. The predefined number of images may be selected according to a third selection method to summarize the subset of images. According to some aspects, the third selection method may select images of the subset of images which are determined or estimated to be of the most interest. For example, in a colon procedure, images of the received stream or set of images, which are identified to include polyps at some level of certainty may be selected according to the first selection method for the subset of images.

Five images of the subset of images, which were identified to include the five largest polyps, or five images which were identified to include polyps in the highest level of certainty, may be selected according to the third selection method. Each image selection method described herein may include one or more filters or selection or detection rules and the selection according to each method may be performed in one or more stages. The selection or detection rules may be applied by utilizing algorithms, e.g., machine learning algorithms and deep learning algorithms in particular. For example, when selecting the subset of images from the received stream of images, detection of one or more features of interest may be performed at a first stage. Different rules (e.g., algorithms) may be used for detection of different types of features, such as different pathologies or passage between different anatomical portions of the GIT. Typically, the results of detection algorithms may be scores assigned to the image indicating the level of certainty that an image includes the detected feature. The relation or filter on which the second selection method is based may produce different corresponding additional images for different first level images or images of the subset of images. At least the first selection method may be based on deep learning techniques, e.g. neural network techniques. The first selection method and the second selection method may each include one or more selection rules.

At a second stage images may be selected from the stream of images based on the detection results of the first stage. The selection may include, for example, different selection rules for different types of features, such as different types of pathologies and passage between anatomical portions. Selection rules at the second stage may be based, inter alia, on threshold determined for the detection scores. For example, for an SB procedure, different rules may be determined for selecting images for the subset of images at the second stage and based on: type of pathologies or features identified in the images, type of spread of the identified pathologies along the GI tract (e.g. focal, diffusive or 'carpet-like' distribution), and the severity or the location of the identified pathologies. The rules may be also based on a maximum number of images to be displayed per a specific feature, per a type of a feature and/or per the entire set of images to be selected. For example, for a focal pathology, a system may select only one image representing the pathology to appear in the subset of images (e.g., one rule). For a diffusive pathology, a system may select a number of images to represent the pathology in the subset of images (e.g., another rule).

As another example, in a colon procedure used as a cancer screening tool, the features of interest may include only one pathology: polyps. Following that, a system may include a rule according to which one image is selected for the subset of images for each identified polyp. An identified polyp may be determined according to a threshold for the image's polyp detection score. Alternatively, or in addition, another rule may be determined, according to which the first subset will include a maximum number of images (e.g., 50, 100, 160, 200 or a maximum number in the order of tens, a maximum number in the order of 100 or a maximum number in the order of a few hundreds). If the two rules are applied, and the number of images selected according to the first rule exceeds the maximum number determined according to the second rule, a third rule may be applied. Such a third rule may determine that the maximum number of images according to the second rule of images selected according to the first rule having the highest detection score are selected for the subset of images. Images of identified polyps having a higher detection score may be considered as more important, for example, since the probability that such images exhibit polyps are higher.

According to some aspects, a rule based on tracking features, such as ulcers of polyps, may be included. Such a rule may be applied in an additional stage. Such a rule may allow identification of images imaging the same specific feature (e.g., the same polyp). Such a rule may be used in the second selection method to determine one or more images showing at least a portion of the same feature shown in an image of the subset of images. Such feature tracking may be performed, for example, based on methods such as disclosed in U.S. Pat. No. 9,430,706, incorporated herein by reference in its entirety, or optical flow techniques.

A system may create or generate a study of the capsule endoscopy procedure, for example, by utilizing methods described herein. The study may include at least the selected subset of images (e.g. a level one view) and optionally additional information. The additional information may include for example one or more additional images selected (e.g. by the system) corresponding to each image of at least a portion of the "level one" subset of images. The additional information may further include information such as localization of displayed images along the GIT, indication of the location and/or type of the identified or suspect features in displayed images, indication of extent of identified of suspected features or type of features along the GIT (e.g., extent of a "carpet-like" pathology or a diffusive disease), indication of segmentation of the portion of the GIT which is of interest, indication of anatomical portions of the GIT and display of images representing anatomical passage between different anatomical portions of the GIT. According to some aspects, a portion of the additional information or all of the additional information may be displayed only upon a user input, e.g., upon a user request via an action (e.g., by activating a control or hovering over a specific display area). According to some aspects, the level one images and/or the level two images may be displayed in a still manner. Typically, level two images are not displayed only when a user selects a level one image for additional review. Typically, a set of second level images includes one or more images which are not included or displayed as first level images. The study images may be displayed in the same view (e.g., when displayed in the same window), as, or in a different view (e.g., when displayed in a pop-up window) from, first level images.

A study may be displayed for a user's review in one or more views. Each study view may include at least the display of the subset of images. Different study views may be characterized in, for example: image display layout (e.g., a matrix or a carousel), image display browsing (e.g., still manner or video), which additional information of the study is displayed (if at all) and the manner the additional information is displayed. For example, according to some aspects, two study views may be displayed. One view includes a display of the subset of images, (e.g., "first level" or "level one" images) in a matrix layout in a still manner with additional information (e.g., GIT segmentation and cleansing level of segments) but does not include the display of the one or more images corresponding to images of the subset of images (e.g., "level two" or "second level" images). A second view may include the display of the subset of images in a carousel layout and the display of all of the additional information included in the study, including the second level images. In case of multiple study views, one view may be defined as the default study view. The default study view, as opposed to the other study views, is not selected by the user for display. Once a specific procedure is selected for study review, the default study view would be displayed. Thus, the default study view is the first study view to be displayed. In case of a single study view, the single study view is the default study view.

A study view may include one or more views. The subset of images is displayed in a main or default view of the study view. The main or default view of a study view may further include the display of additional information, such as a map localizing the images of the subset of images along the GIT, a cleansing level indication for each image of the subset of images, a segmentation of the portion of interest of the GIT, capture time of the images of the subset of images and/or estimated transit time of the GIT portion of interest (e.g., an estimation of the time it took for the capsule device to transverse the GIT portion of interest). Other additional information may be displayed only upon receipt of user input, such as the display of the additional one or more images corresponding to images of the displayed subset of images. Such "optional" display of information (e.g., its for the user to decide if this additional information is displayed or not) may be in the main view or in a separate view. For example, the additional one or more images corresponding to images of the subset of images may be displayed in the main view, e.g., in the same image window in which the corresponding image of the subset of images is displayed or in a different dedicated area of the main view of the study view. In another example, the additional one or more images corresponding to images of the subset of images may be displayed in a separate view, such as in a pop-up window.

A study display or view may include multiple characteristics. A study display characteristic may include the manner of displaying the subset of images, a layout for the display of the images (e.g. carousel or matrix), including the number of images displayed simultaneously; the manner of browsing between the images (if not all of the images are simultaneously displayed); and a display of additional information. For example, a characteristic may include which additional information may be displayed in a specific display or view and which is not. Characteristics referring to the display of additional information may include the determining of which information is displayed by default in a specific view and which is displayed in the specific view only upon user request (e.g., the display of indication to a feature in an image). A study display characteristic may specifically include a layout of display of second level images, e.g., in a carousel manner or as a video clip, in the same window as the first level images or in a pop-up or another window or screen, one at a time or simultaneous display of a few images. According to some aspects, browsing between images in a set of images displayed may be per an image (e.g., each browsing action replaces only one image currently displayed) or per a page or a screen (e.g., in case multiple images are displayed simultaneously, each browsing action replaces all of the images currently displayed), in a still manner (e.g., where browsing between images or pages of images is performed only per a user input) or in an automatic manner (e.g., when the user activates a browsing control and the browsing is performed automatically between images or pages of the set of images displayed). According to some aspects, the display of images, e.g., the selected subset of images, is per a segment of the portion of interest of the GIT and based on segmentation of this portion. For example, in a study view, the set of images may be displayed per a segment, where each segment is displayed by activating a tab. According to some aspects, some display or view characteristics may be predefined by the user or may be changed upon user input (e.g., number of images displayed simultaneously in a view). In some embodiments a user may browse or cause a display to move between images or between "pages" of sets of first level images (e.g., if a display includes x images then browsing to the next page would present the next x images). Automated browsing (as opposed to video display) may move to the next image or next "page" automatically.

In one embodiment, in a view or display of second level images only one image is displayed at a time (as opposed to the first level images, where multiple first level images are displayed at once). Second level images may be displayed as a video clip, e.g. using an auto-play mode.

A study may include all the images and information provided to the user by a system, for example all the data related to a case or procedure presented to a doctor, including image time of capture, images (e.g. first and second level) and additional data such as the result of analysis of data related to the case and/or procedure a system may perform. A study may also include patient information (e.g. details, background, history).

According to some aspects, an embodiment of a system may display on a display device (e.g. a monitor) the subset of images for the user's review: typically the displayed images are one or more representative images per group, and thus each of the different groups may have one or more representative images displayed in a "first level" display. The first level display may display these images by "default", e.g. without user input or selection, and this first level display may display images in a still manner, rather than moving images or movies.

Images of the first level or "representative" images, which are captured by a single imaging device of the capsule device used in the procedure, may be simultaneously displayed. The number of images or the maximum number of images which may be displayed simultaneously in a view or display, e.g. of images of the first level, may be predefined.

According to some aspects, a study includes first level information which is displayed in a default view of the study. Thus, the display of the first level information is mandatory and its not for the user to decide if this type of information is displayed or not. According to some aspects, the first level information consists only of the selected subset of images representing the stream or set of images received from a capsule device or from a receiving device. A study may also include a second level information. The second level information may be displayed only upon user input (e.g., per a user's request) and thus its display may be optional. The second level information may provide information additional to the first level information. The second level information, or at least a portion of it, is associated with or corresponds to images of the subset of images.

Such selection and display of procedure related information may allow to make the review process by a user more efficient, may reduce review time and lead to better diagnosis. According to the present methods and systems, a user may review the study in a manner that suits his skills and preferences and/or the needs deriving from the specific patient, procedure and/or study. In that manner, the disclosed systems and methods may allow for a personalized review of a procedure study. For example, a skilled user may require less information to make a diagnosis than a novice user. Accordingly, the novice or less skilled user may choose to display and review additional information which is not required for the skilled user. As another example, review of a study of a procedure performed in a subject which is believed and/or known to be sick may involve a display of more additional information that the review of a study of a procedure performed in a subject believed and/or known to be healthy.

Furthermore, additional information, which is not typically or which was not so far displayed or provided to a user in the frame of a study of a CE procedure, may be provided according to embodiments of the described systems and methods. Such information may help and support the user in making diagnosis and/or therapeutic decisions, which may lead to faster and better diagnosis and care. The additional information includes information which was generated or achieved, inter alia, by employing state of the art computer-aided-decision making technologies, such as deep learning techniques.

According to some aspects, to display second level information, a user may select (e.g. by providing user input to the Graphical User Interface (GUI)) one image in the first level display, the image corresponding to a group of images, and thus may correspond to other, not yet displayed images in that group. According to some aspects, all images in a group may include or image the same automatically found feature of interest, and thus the images in the group other than the single image displayed in the first level (images corresponding to the first level image) may show the same feature shown in the image displayed for that group in the first level. Upon receiving the user input regarding a first level image, the system may display the one or more images corresponding to the selected first level image of the subset of images which is currently displayed. This may cause a second level display of additional information. For example, the group of images selected may be displayed in a still manner, the user may be then able to scroll through the group of images causing images in the group to be displayed in sequence, or another display method may be used, such as displaying the group of images as a video clip. During the display of images, the user may add or annotate information with respect to an image displayed. After the user finishes reviewing the images, the system may create or generate a report including images from the displayed images selected by the user, and no other images. In some embodiments, the report may include only images viewed by the user, and possibly user-input information, and no other images of the captured stream of in-vivo images. Typically, only the selected subset of images and images corresponding to images in the subset are available for display for the user's review in the report.

According to some aspects, an interim study may be displayed and optionally generated by the disclosed systems and methods. An interim study may be generated based on a partial stream or set of images received from a capsule device or from a receiving device communicating with a capsule device. The partial stream of images may include only images which were captured until only a certain point in time with respect to the commencing of the procedure (e.g., the subject swallows the capsule) or until a certain location within the portion of interest of the GIT is reached by the capsule and prior to the end of the procedure. The partial stream of images is received, the generation of the interim study is performed and the review of the interim study is done by the medical professional typically during the procedure. According to some aspects, the interim study is generated and displayed before the capsule device reaches the end of the portion of interest of the GIT. The generation and display of the interim study for a user's review may be performed by the disclosed systems and according to the disclosed methods with the required changes. An interim study may include a subset of images selected from the partial stream of images received. An interim study may typically include less additional information comparing to the complete study (e.g., the study). For example, in some embodiments an interim study does not include a second level images. A user may then generate an interim report based on the interim study by using the systems and methods disclosed herein. An interim study may be used to provide a required medical diagnosis and treatment, including referring the patient to go through a medical procedure to be performed at the same day or shortly after the CE procedure is complete.

For example, a patient may be referred to a same day colonoscopy if a polyp that should be removed is identified by the medical professional while reviewing the interim study. A same day colonoscopy may have advantages, including saving the patient another colon preparation. According to some aspects, a user may determine parameters such as the certain point in time or the certain location within the portion of interest of the GIT that determines the partial stream of images from which the interim study is generated. According to some aspects, a user may select a time of the day at which he will receive the interim study.

A last image may be displayed. The last image may be the last image captured by the capsule or the image identified to be located at the last location captured by the capsule (note a capsule may go back and forth). This may be displayed, for example, to let the doctor know up to where the capsule captured images and if portions of interest were reached. The last image may be part of the subset of images or may be part of the additional information.

According to some embodiments, images captured in vivo may be received and a plurality of these images may be automatically (e.g. by a processor shown in FIG. 1) selected for display. In some embodiments, a subset of these selected images may be identified automatically and/or by a user and a case report or a report may be generated which includes only images from the identified subset of images (e.g., one or more or all of the images in the subset).

The images selected for display may be, for example, images which are suspected to include specific pathologies, anomalies or anything out of the ordinary and/or images selected to represent or exhibit a certain portion of the GIT or a certain anatomical area of the GIT.

The disclosed systems, methods and computer program products may be realized or executed via one or more software applications that may receive or may have access to the selected images and/or to the entire stream of images captured in-vivo and/or to a portion of it. Such applications may, for example, display the selected images to a user, interact with a user (e.g., via a GUI), facilitate analysis of the displayed images by the user, provide automatic analysis of the displayed images, and/or generate a report. According to some embodiments of the disclosure, such applications may perform the selection of the images to be displayed. The systems and computer program products according to the present disclosure may include one or more non-transitory computer-readable storage mediums (which may also store data such as images, a stream of images, etc.). The systems according to the present disclosure may include one or more hardware processors, one or more displays, one or more I/O devices and/or one or more communication devices utilizing one or more communication technologies. The one or more software applications may include program code stored in the one or more non-transitory computer-readable storage mediums and executable by the one or more hardware processors. The images and/or any further data may be displayed to the user via the one or more displays and the user may interact with the one or more applications via the one or more I/O devices. The stream of images, a portion of it or a selected subset of the stream of images may be received or remotely accessed (e.g., via the internet) by the one or more communication devices.

FIG. 1 shows a high-level block diagram of an exemplary computing device which may be used with embodiments of the present invention. Computing device 100 may include a controller or processor 105 that may be or include, for example, one or more central processing unit processor(s) (CPU), one or more Graphics Processing Unit(s) (GPU or GPGPU), a chip or any suitable computing or computational device, an operating system 115, a memory 120, a storage 130, input devices 135 and output devices 140. Modules or equipment collecting or receiving (e.g. a receiver worn on a patient) or displaying or selecting for display (e.g. a workstation) medical images collected by a swallowable endoscopy capsule may be or include, or may be executed by, a computing device such as included in FIG. 1. Communication element 122 may allow communications with remote or external devices, e.g. via the Internet or another network, via radio, etc.

Operating system 115 may be or may include any code segment designed and/or configured to perform tasks involving coordination, scheduling, arbitration, supervising, controlling or otherwise managing operation of computing device 100, for example, scheduling execution of programs. Memory 120 may be or may include, for example, a Random Access Memory (RAM), a read only memory (ROM), a Dynamic RAM (DRAM), a Synchronous DRAM (SD-RAM), a double data rate (DDR) memory chip, a Flash memory, a volatile memory, a non-volatile memory, a cache memory, a buffer, a short term memory unit, a long term memory unit, or other suitable memory units or storage units. Memory 120 may be or may include a plurality of, possibly different memory units. Memory 120 may store for example, instructions to carry out a method (e.g. code 125), and/or data such as user responses, interruptions, etc.

Executable code 125 may be any executable code, e.g., an application, a program, a process, task or script. Executable code 125 may be executed by controller 105 possibly under control of operating system 115. For example, executable code 125 may when executed cause the display or selection for display of medical images as described herein. In some embodiments, more than one computing device 100 or components of device 100 may be used for multiple functions described herein. For the various modules and functions described herein, one or more computing devices 100 or components of computing device 100 may be used. Devices that include components similar or different to those included in computing device 100 may be used, and may be connected to a network and used as a system. One or more processor(s) 105 may be configured to carry out embodiments of the present invention by for example executing software or code. Storage 130 may be or may include, for example, a hard disk drive, a floppy disk drive, a Compact Disk (CD) drive, a CD-Recordable (CD-R) drive, a universal serial bus (USB) device or other suitable removable and/or fixed storage unit. Data such as instructions, code, medical images, image streams, etc. may be stored in a storage 130 and may be loaded from storage 130 into a memory 120 where it may be processed by controller 105. In some embodiments, some of the components shown in FIG. 1 may be omitted.

Input devices 135 may be or may include for example a mouse, a keyboard, a touch screen or pad or any suitable input device. It will be recognized that any suitable number of input devices may be operatively connected to computing device 100 as shown by block 135. Output devices 140 may include one or more monitors, screens, displays, speakers and/or any other suitable output devices. It will be recognized that any suitable number of output devices may be operatively connected to computing device 100 as shown by block 140. Any applicable input/output (I/O) devices may be connected to computing device 100, for example, a wired or wireless network interface card (NIC), a modem, printer or facsimile machine, a universal serial bus (USB) device or external hard drive may be included in input devices 135 and/or output devices 140.

Embodiments of the invention may include one or more article(s) (e.g. memory 120 or storage 130) such as a computer or processor non-transitory readable medium, or a computer or processor non-transitory storage medium, such as for example a memory, a disk drive, or a USB flash memory, encoding, including or storing instructions, e.g., computer-executable instructions, which, when executed by a processor or controller, carry out methods disclosed herein.

Multiple computer systems including processors, etc. such as in FIG. 1 may be used: e.g. a capsule, a receiver, a cloud-based system, and/or a workstation or portable computing device for displaying images may include components of FIG. 1. A cloud platform (e.g. a remote server) including components such as in FIG. 1 may receive procedure data such as images and metadata, process and generate a study, and may also display it for the doctor's review (e.g. on a web browser executed on a workstation or portable computer). An "on-premise" option, may use a workstation or local server of a medical facility to store, process and display images.

According to some embodiment of the disclosure, a user, e.g., a physician, may build his or her understanding of a case by reviewing a display of still images (e.g. captured by a swallowable capsule) that were selected, e.g., automatically, as images that may be of interest. A case may be, for example, the images captured during the passage of a capsule endoscope through the gastrointestinal tract (GIT) or a portion of it (e.g., the small bowel and/or the colon) of a patient. The still images may be displayed in one or more screens and may be arranged in various layouts (e.g., in a matrix, in a row, in a column and/or in or over an illustration of the GIT or portions of it). According to some embodiments, the display of still images may be the default study display or study mode or view. According to some embodiments, the images are displayed only in a still manner (as opposed to a stream of images or a video). The user may browse between the still images (e.g., images displayed in a still manner), for example, by scrolling between one or more images (e.g., between groups of images). In some embodiments, the still images may be displayed horizontally to simulate the elongated structure of the GIT. Such display may ease the review task for the physician. The number of still images simultaneously displayed may be predetermined or pre-selected by a user. In some embodiments, the number of images displayed simultaneously may be changed by the user. In some embodiments, the number of images displayed simultaneously may be between three to seven images.

According to some embodiments of the present disclosure, a relatively small number of images from the captured images is displayed for the user's review per a case. By "relatively small number" it is meant on the order of hundreds at most or at least at average as opposed to current methods, which display a video stream of images that typically includes thousands of images per a case (e.g., around 6,000 images). In some embodiments, only up to a few hundreds of images are displayed for the user's review. In some embodiments, the number of images displayed for the user's review is up to an order of 1,000 (i.e., below 2,000 images per a case).

Browsing through still images (e.g., images displayed in a still manner) may allow the user more control of the time and manner of display of each image and/or of each group (or array) of images as opposed to watching or reviewing a video stream (e.g. a movie) of images. Browsing through a relatively small amount of still images, as opposed to watching or reviewing a video stream of thousands of images, may significantly ease the review process for the user, reduce the reading time per a case and may lead to better diagnosis.

Selection of only a relatively small number of images for display and review per a case or a study may be enabled, inter alia, by utilizing selection or decision-making methods which provide high sensitivity (e.g., by providing high probability of identifying the images of interest) together with high specificity (e.g., by providing high probability of identifying images which are not of interest) per a case. According to some embodiments, image selection may be performed by utilizing state of the art methods such as deep-learning methods.

In some embodiments according to the disclosure, additional information referring to the capsule endoscopy procedure (e.g., except for the selected images) may be displayed. The additional information may be displayed as a default (e.g., in the default screen) or may be optional and displayed per the user's request or following a user's action or input.

In some embodiments, the additional information may refer to a currently displayed image or currently displayed group of images. For example, a user may indicate a still image or a plurality of still images currently displayed to receive additional information referring to the indicated image/s. The additional information may include, for example, one or more of the following: one or more images surrounding or adjacent to the indicated image/s, indication of an area of interest within the indicated image/s and/or the type and/or size of pathology/ies and/or any other structure or feature of interest the indicated image/s is/are suspected or identified (e.g., at some level of certainty) to include.

In some embodiments, the display of a case (e.g. a set of images taken from a patient during one pass of a capsule through the patient or a procedure) may include two levels or categories of information which may be displayed separately or together, depending on user input and settings: a first level (e.g. "level one") including a default display (e.g. the main view of a study default view) in which selected still images are displayed by default for the user's review and a second optional level (e.g. "level two"), which includes a display of additional information and may be displayed per the user's request or following a user's action.

A default or first or main screen or display (e.g., of a default study view) may include "first level" images of a case, which may have been automatically selected as images of interest, for example images showing a pathology (with some level of certainty). In some embodiments, if multiple images are identified as capturing a specific pathology (e.g. ulcer), only one of those images may be selected to be presented in the default or main screen (e.g. first level images). Other features or structures may be identified as structure of interest, separate from a pathology (e.g., certain anatomical structure or a foreign body, an anomaly, a combination thereof, etc.). A user may select an image from the first level and "activate" it to watch images of a second level, related to the first level selected image. For example, if a user selects (e.g. clicks or hovers on or otherwise indicates) an image of an ulcer from a first level display, then in the second level, for example, the user may scroll between other images of this ulcer (that may precede and/or follow the selected image).

In some embodiments, the option to display (e.g., via controls) or a display of second level or category information with respect to a first level image in-focus (e.g., an image selected by the user) may be performed via a separate window or screen (e.g., a pop-up window). Typically, such a separate window or screen would appear upon a user's request or action, e.g. upon the receipt of user input regarding an additional level of display or category. In some embodiments, the first level image in-focus is displayed together with its associated second level images in a separate view, e.g., a separate window or screen. A separate window or screen may provide more screen area for display of the image in-focus and its associated second level information.

In some embodiments, the second level of information and/or controls for displaying second level information may be presented in the same initial or default screen: e.g. a GUI item allowing user input to request a second level of display, or to control that second level after it is displayed, where the second level display may appear with the first level of display, e.g., in the same screen or display area or in a dedicated screen or display area. In such embodiments, no separate windows or screens are required or displayed to present the second level of information. By providing the second level of information in the same screen or window with the first level or default information, it allows the user to stay in context and thus may facilitate and better the review process.

In some embodiments the second level of information may include additional images. The additional images may be also selected from the received series or set of captured images. In some embodiments, the second level of information may include a plurality of images surrounding one or more still images displayed on the first level and indicated by the user. The surrounding images may be selected according to their capture time with respect to the capture time of the indicated image(s) and/or according to their location along the imaged GIT portion with respect to the location of the indicates image(s). In some embodiments, a predetermined number of images most adjacent to the first level indicated image(s) may be displayed in the second level. In some embodiments the second level display may include a display of the indicated first level image(s) and images which surround or captured around the capture time of the indicated first level image(s). In some embodiments, the second level display may be combined for two or more images of the first level, e.g., in case two images in the first level are estimated to be located adjacently in the imaged GIT portion. In some embodiments the additional images and the indicated images may be displayed in the second level as still images and/or as moving images (e.g., as a video clip, moving image sequence, or movie).

In some embodiments according to the present disclosure, the still images may be displayed in a localized manner, e.g. along with location information providing the location of the site of capture of the image within the GI tract. In some embodiments all of the images selected for display may be displayed in a localized manner. In some embodiments, the localization of the images may be provided only per the user's request (e.g., as part of the second level of information). Typically, a user request, or a user selection, or a user change in mode, or other input, is received as input at a computing device (e.g. as shown in FIG. 1, via an input device). In some embodiments, only images selected by the user as images of interest, e.g., images identified by a physician as depicting polyps in a colon procedure, are displayed in a localized manner. The localization of a finding or pathology may provide important information which may influence, for example, the therapeutic decision or provided treatment. Thus, for example, a location of an identified polyp may determine if a sigmoidoscopy or colonoscopy should be performed to remove the polyp and may guide the physician while doing so.

The imaged GIT portion may be divided into segments. For example, the small bowel may be divided into three segments equal in length, for example, according to methods disclosed in the US Patent Publication 2019/0244351, incorporated herein by reference in its entirety or other known methods. The colon may be divided, for example, into five anatomical segments: cecum, ascending or right colon, transverse colon, descending or left colon or left colon—sigmoid and rectum, or into two anatomical segments separated by the splenic flexure for example based on methods disclosed in http://www.cs.technion.ac.il/~cs234313/projects sites/S18/12/site/ incorporated herein by reference in its entirety. The display of the images (e.g., first level images, second level images or both) may include indication in which segment each image is located. In some embodiments, the location of each image within a segment may be indicated. In some embodiments, the identified area of interest (e.g., an identified feature of interest in an image) or its location (e.g., location within the image) may be indicated in the image. For example, a contour may delimit the identified area, or an arrow may indicate the location of the identified area in the image. The location of the images along the imaged GIT portion may be determined by known methods of location estimation. For example, the location of the images along the imaged GIT portion may be determined based on a computerized assessment of the capsule device progress through the subject's GIT. Such computerized assessment may be based, for example, on the methods and systems disclosed in U.S. Pat. No. 8,792,691 to Krupnik et al., entitled "System and method for detecting motion patterns of in vivo imaging devices", assigned to the common assignee of the present application, or other known methods.

In general, the division of the GIT into anatomical segments may be performed, for example, based on identification of the capsule endoscope passage between the different anatomical segments. Such identification may be performed, for example, based on machine learning techniques.

In some embodiments a map representing at least the entire imaged GIT portion or a section of it may be displayed. The map may include indications of the selected images (e.g., of first level images and/or second level images). Accordingly, the map may provide to the user an overview of the imaged GIT portion or a section of it, with respect to suspected areas or areas that might be of interest, their extent (e.g. their occurrence along a length of the GIT) and/or their distribution. Extent may be estimated or generated automatically by the system, and presented to the user visually (e.g. an indication of the length on a map) or numerically (e.g. a dimension of the extent, such as by percentage). The map may be used by the user to navigate between the selected images. In some embodiments the map may be in the form of a bar or in a form similar to the form of a GIT. In some embodiments the indication of the selected images may be in the form of a heat map, an abstracted representation of all or a portion of the GIT, such as bar displaying selected images according to their location along the GIT. "Heat" may refer to colors used to convey information on the map, such as colors assigned to lines signifying certain images along the bar. Different colors may represent, for example, different type of images, such as images of a first or second level. Such a heat map or bar may include lines indicating the segmentation of the GI portion (e.g., colored in a different color) etc. Colored sections of the map may provide certain information about those sections. A system or GUI may receive a user's selection of an image indication or position in the map, and in response display the image represented by the user selected image or position indication or additional information referring to the map indicated image.

The indication of the selected images in the map may be according to their estimated location along the imaged GIT portion. In some embodiments, the segments of the imaged GIT portion may be indicated in the map. In some embodiments, the currently displayed segment (i.e., the segment in which the currently displayed images are located) may be indicated in the map (e.g., by coloring or highlighting the segment). The selected images may be indicated in the map based on their chronological order. In some embodiments, the image in-focus may be indicated in a map. The user may select an image to be displayed or an image to be on focus from a map.

In some embodiments, the map may include indications of the type of features or structures of interest identified along the GIT portion represented by the map. The indications may be, for example, icons representing the type of feature (e.g., bleeding, ulcer or polyp).

In some embodiments the map and/or graphical representation may be displayed above the selected images and/or on the top section of the screen. Such a top display may facilitate navigating through the selected images via the map (e.g., the user would not be required to move his gaze, e.g., lower his gaze, to view the map).

A cleansing or cleanliness level which may be provided or displayed by embodiments of the invention may describe the cleaning level of the bowel with respect to content, feces and food residue, typically after "preparation" prior to examination procedures such as capsule endoscopy, the preparation procedures intended to cleanse the GI tract from such visual obstructions. A known standard for a colon cleansing level includes 4 levels (other numbers of levels or standards may be used). Several methods to evaluate the cleansing of the small bowel also exist; in one embodiment the cleansing standard for colon may be used to describe the cleansing level of the small bowel.

In some embodiments the additional information may include an indication or a graphical representation of a cleansing level of the images which provides indication of the cleansing level of the imaged portion of the GIT. The cleansing level may be estimated or determined (e.g. automatically by a system such as in FIG. 1) for each image of the captured sequence of images or only for each image of the selected images and/or for each segment of the imaged GIT portion and/or for the entire imaged GIT portion. In general, the imaged GIT portion may include matter such as content (e.g. matter naturally occurring in the GIT which may obscure imaging) and/or bubbles which may obscure the tissue of the GIT. The images may be then analyzed to detect such obstructing elements. A score may be assigned to each image indicating the level of cleansing detected in the image. In some embodiments the cleansing level may be presented in the form of a graph or a bar, e.g., a color bar. In some embodiments the cleansing level graphical representation may be displayed beneath the map or above the map and in a corresponding manner. In some embodiments, some categories may be determined, such a low cleansing level, medium cleansing level and high cleansing level and the cleansing level of the images may be determined according to these categories.

In some embodiments a score may be automatically (e.g. by a system as shown in FIG. 1) determined and assigned to each image or each selected image and/or segment and/or procedure which may reflect the mucosal coverage of the imaged section of the GIT (e.g., the colon). A procedure for this matter may be a set of images captured by a specific capsule once swallowed by a specific patient at a specific time instance. For example, such a score may reflect how much (e.g., in percentage) of the tissue (mucosa) of the GIT section was captured by the images. Such a score may be based on, for example, estimated or determined cleansing level, content, bubbles, capsule transit time, capsule velocity and/or capsule dynamics. The score may provide information to the physician or viewer with respect to the adequacy of the procedure. This score may be provided in addition to the cleansing level or instead and may be displayed in a similar manner as described above with respect to the display of the cleansing level. The score may be provided to the user by default or upon request, before the review of the selected images, during and/or after the review of the images.

In some embodiments, the additional information may include a sequence of images in the captured series of images identified to include the passage between anatomical segments or anatomical sections of the imaged GIT portion. Such a passage may be, for example, the passage from the stomach to the small bowel, the passage from the small bowel to the colon or the passage from the colon to the exterior of the patient's body. In some embodiments, the additional information may include only a representation of such a sequence of images (e.g., a summary of the images). In some embodiments, the representation of this passage sequence of images may include a color bar. Such a passage representation may allow the user to more closely review the passage between the different anatomical sections of the imaged GIT portion. In some embodiments, the passage sequence of images or a representation of such, may be displayed upon the user's request or following a user's action, e.g., hover over an indication of such passage, e.g., in a map representing the imaged GIT portion. In some embodiments, such an anatomical passage may be a feature of interest to be identified and represented in a first level or the selected subset of images. For example, a single image may be selected to represent the passage in the subset of images (e.g., first level images) and the one or more image associated with the selected image of the subset of images (e.g., second level images) may be additional images selected to represent the passage.

In some embodiments, automatic size estimation of features, pathologies or any other finding automatically identified in an image and/or indicated by a user in an image, such as polyps, may be provided. Automatic size estimation may be provided as additional information, e.g., second level information, and/or upon a user's request and not by default. In some embodiments, an indication of an area of interest and its size estimation may be provided by default. According to some embodiments, the automatic size estimation may be based on known size estimation methods which, for example, provide size estimation based on user input. The user input may indicate at least one dimension of the feature to be measured as shown in the image, e.g., a length or a diameter represented for example by two or more image pixels indicated by the user. Such methods may be found in U.S. Pat. Nos. 9,412,054 and 9,911,203 incorporated herein by reference in their entirety; other known methods may be used. To generate a complete automatic size estimation, an automatic estimation of the user input may be then generated. For example, by segmenting the identified feature of interest in the image and selecting two edge points or two perimeter points of the segmented feature which are the most distant from each other. In some embodiments, the user may correct or replace the two points automatically selected and receive a size estimation based on the input provided by the user.

In some embodiments, an automatic interim report may be generated during the capsule endoscopy procedure. Such automatic interim report may be based, for example, on the images captured up to a certain time and/or based on images of a certain identified anatomical region of the imaged portion of the GIT and/or based on images of a specific finding, e.g., a meaningful finding such as a major bleeding or a polyp which needs to be removed. The interim report may be generated, for example, after a pre-determined period has passed since the capsule endoscopy device was swallowed by the patient or since it has been identified that the capsule endoscopy device has reached an anatomic landmark (e.g., the beginning of the small bowel or the beginning of the colon). As another example, the interim report may be generated once it has been identified that the capsule endoscopy device has reached a certain anatomical landmark or once a certain pathology or event was identified, such as a bleeding or a polyp. The interim report may be then provided to the assigned physician.

An automatic interim report may include images selected to represent the set of a stream of images received and/or a specific finding. In some embodiment, the automatic interim report may also include additional information as disclosed herein. In some embodiments, the automatic interim report may include an indication to specific finding and a suggestion for diagnosis and/or a suggestion or recommendation for treatment or therapeutic course of action.

In some embodiments, the generation of an automatic interim report or of an interim study for the medical professional to review according to different embodiments, indicating, in real time, an identified pathology or any other finding which may require a medical intervention (such as a surgery or minimally invasive procedure), may allow the performance of such a procedure without delay, e.g., immediately or as soon as the capsule endoscopy procedure ends or shortly after that. In some cases, an immediate medical intervention may be required, e.g., in case of a major bleeding. However, even when the required medical procedure is not urgent (e.g., in a case a polyp which needs to be removed is identified), the interim report may allow utilizing the fast and/or bowel preparation performed by the patient for the capsule endoscopy procedure for the required medical procedure, e.g., by performing colonoscopy at the same day. Same day colonoscopy, for example, may be more convenient and less difficult to the patient which will not have to go through preparation twice.

The generation of an automatic interim report or of an interim study in real-time and during an active procedure may be facilitated, for example, by utilizing technologies such as distributed computing, decentralized computing and/or cloud computing. In some embodiments, an automatic interim report or an interim study may include a score referring to the estimated or determined cleansing level or to the adequacy of the procedure up to this stage, as described in the present disclosure. Such information may be used by the physician to provide instructions and/or change the instructions provided to the patient with respect to preparation and/or diet in case it was decided to perform a following medical procedure (e.g., same day colonoscopy).

Embodiments may apply to the display of still images and/or moving images (e.g., a video), mutatis mutandis. In some embodiments, the additional information included in a study according to the systems and methods disclosed herein, may include a suggestion for diagnosis and/or a suggestion or recommendation for treatment or therapeutic course of action. Such suggestions may be based on the processing and analysis performed by and according to the systems and methods disclosed herein and may be based on the relevant standard of care.

In one embodiment, the selection of images of interest to be displayed for a user's review is performed in two stages. In a first stage, a plurality of images of interest from the captured series of images is automatically (e.g. by a computing device such as in FIG. 1) selected and displayed to the user, e.g., in a matrix, grid or other layout. The selected images may be displayed in a localized manner, e.g. along with location information providing the location of the site of capture of the image within the GIT. In a second stage, the user may select (e.g. by providing user input) images from the automatically selected images to receive a display of additional information with respect to the selected image (e.g., image in-focus). The additional information may include additional images automatically selected. The user's selection of images may be then used to generate or populate a map or a report for the entire case.

Figure 2:
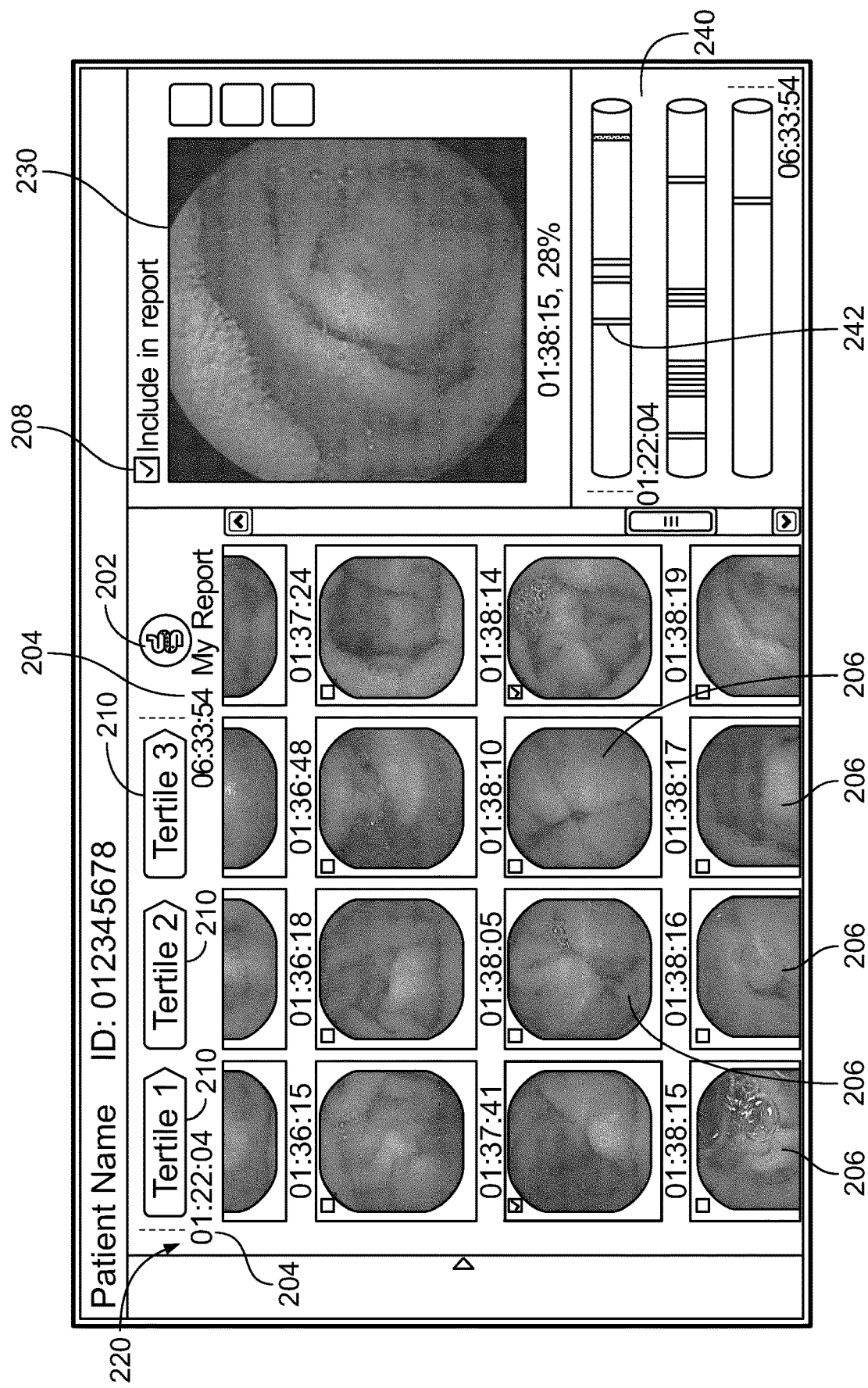
FIG. 2 shows a first screen or a default screen, which is presented to the viewer or user initially, according to some embodiments.

FIG. 2 shows a first screen, e.g., a default screen, which is presented to the viewer or user initially, e.g., as the default screen of a default display of a study. The viewer may navigate between the various regions or segments of the imaged GIT portion, which in the example of FIG. 2 are three tertiles of the small bowel. Each tertile may be represented as one of three tabs 210 on this example screen. When selecting a segment or a small bowel tertile, e.g., by a user clicking the respective tab 210 in the GUI displayed in FIG. 2, images 206 pertaining to that tertile that were selected automatically are displayed to the user, e.g., in a matrix layout 220 at a central area of the screen. In this example, each tertile represents one third of the passage time of the capsule through the small bowel. In some embodiments, each tertile may represent an estimation of one third of the length of the small bowel. In some embodiments, the tertiles may be parsed based on the detection of landmarks along the small bowel. A button 202 may be clicked on or otherwise indicated by a user to toggle between a report screen and a first view. Estimated entry and exit times 204 to the small bowel or other GIT section may be displayed.

In some embodiments, a user may switch between a level one and level two display. For example may switch to a level two display by clicking on an image shown in level one. When selecting a specific image, e.g., by a user clicking on the image when displayed on the GUI, a larger version of that image is displayed in an "additional information" (e.g. second level) area 230 of the screen. Each image of the additional information display may correspond to one first level image in a default view, e.g. by showing the same feature or pathology shown by that first level image. The user can view additional information pertaining to the selected image of images 206 in the "additional information" or second level area, such as additional still images that chronology were captured before or after the selected image or a short clip (e.g. moving image sequence, or movie) including images surrounding (e.g. a few images before or after, or images captured a few seconds before or after) the selected image. In FIG. 2 the second level images are displayed in the same view of display of the first level images. The user can also identify the selected image as an image of interest or otherwise mark it for inclusion in the case report, e.g., by checking a dedicated checkbox 208 which may be located on the selected image in the main display area. Additional functionality may be available to the user on this screen, such as of the option to add markings (e.g. via a user entering information to a GUI) or comments to selected images.

Such a screen or display as in the example of FIG. 2 may include a heat map or other information presentation 240 which may include for example a graphical representation, displaying information in graphical form, of each of the segments or tertiles. When the user selects images of interest, an indication (such as a vertical line 242) may be added on the graphical representation or map of the respective segment at a location corresponding to the location of the selected image within that segment. Indications such as 242, and similar indications shown in other figures, may be localized image indications or markers representing the images according to their location or estimated location in the GIT. This second stage selection, performed by the user, may be separate from or integrated with the user's selection of images for the report as described above. Accordingly, in some embodiments, after the user selects images to populate the map, he may then perform another selection of images to be included in the report. In other embodiments, the images selected by the user to populate the map may be also the images which will be included in the report.

In the example display of FIG. 2, up and down scrolling may be available to the user if the number of the automatically selected images for a segment or tertile is higher than the number of images that fits within the central display region. In the example of FIG. 2, an image chosen by the user for display in the "additional information" area may be highlighted (e.g., by a blue frame) and that the respective marking on the heat map area may also be highlighted at the same time.

Figure 3:
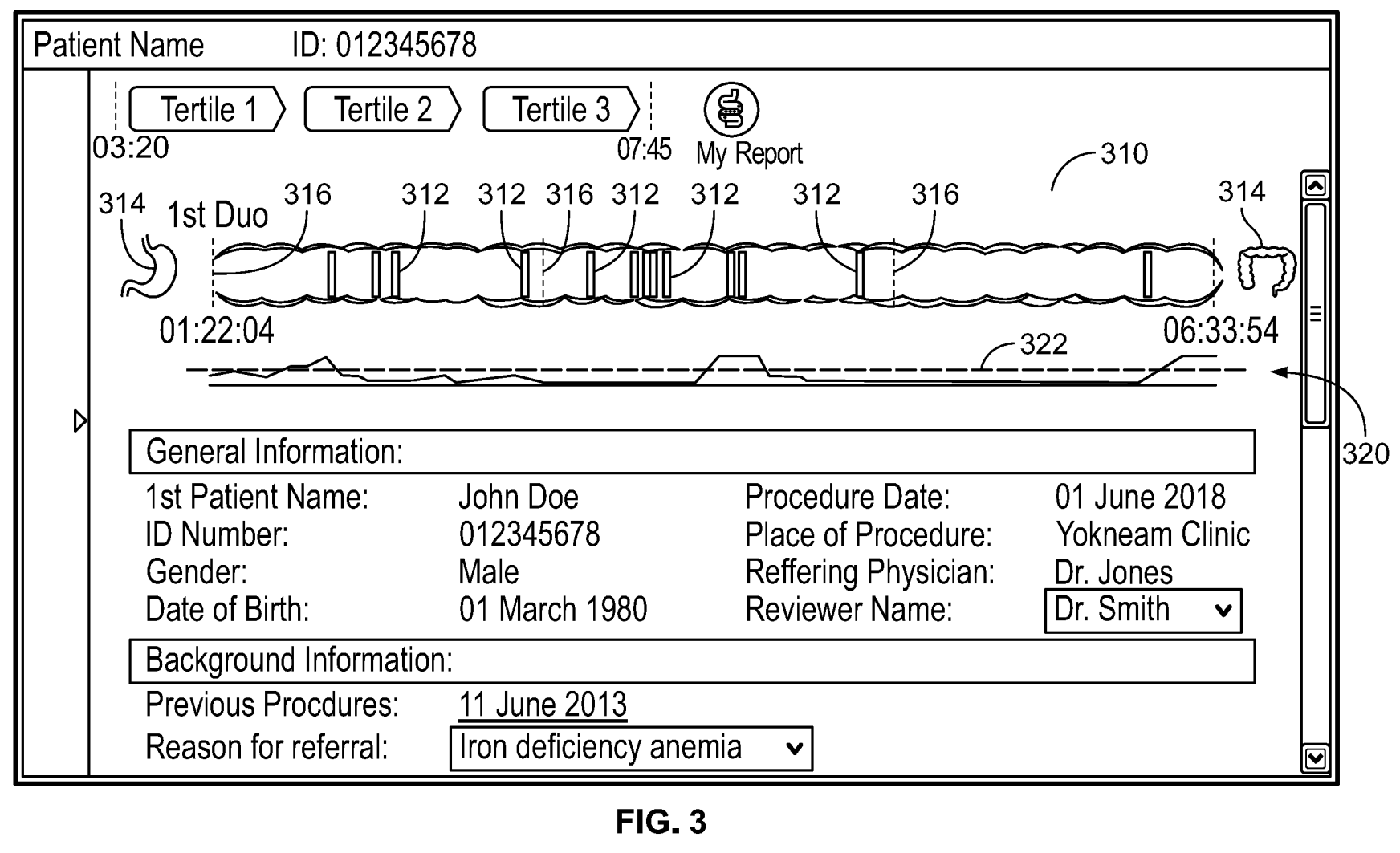

FIG. 3 shows an example screenshot. In some embodiments, a map or a case map generated 310 based on the user's selection of images may be displayed, e.g., in a separate screen as shown in the example of FIG. 3. In the example of FIG. 3 the case map 310 is an elongated bar with various markings, time marks, and other symbols 312 illustrating in graphical form the GIT of the subject of the case (e.g. the person whose GIT was imaged by the capsule). The map may include an illustrative representation of the entire case or substantially the entire case, including the entire imaged GIT portion (which in FIG. 3 is only a portion of the entire GIT). In the example of FIG. 3 a graphical representation of an entire spread out small bowel is displayed, but other illustrative graphical representations of the entire case are possible. In some embodiments, the illustrative graphical representation may include elements 314 resembling or alluding the anatomical features of the relevant segment. For example, the representation in FIG. 3 includes an indication of the preceding and subsequent organs along the gastrointestinal tract (e.g., an image of the stomach and the colon displayed at the respective opposites ends of the small bowel representation).

Alternatively, this screen may display a map that represents the segments more schematically.

Separate markings may be used to delineate the separate segments, such as the three tertiles of the small bowel. In the example in FIG. 3, these markings are broken vertical lines 316 at the beginning and end of the small bowel graphical representation and at equal distances along this representation.

The images selected by the user may be represented by markings on the map. Here, for example, these marking are full vertical lines 312 and the user may access the respective images by for example clicking on or by hovering over these markings.

The map screen or display of FIG. 3 may also include a graphical representation of, or an indication of, an estimated or determined cleansing level, e.g., a score for an automatically measured level of cleanliness of the respective segment, and/or an indication of the image quality during the capsule passage in that segment. Similar indications of cleansing level are shown in other figures herein. The cleansing score may be calculated, for example, based on an automatic estimation of the portion or percentage of the image frames that is covered with content or that otherwise does not show the tissue walls of the respective organ. In this screenshot, the cleansing level is represented as a bar 320 including a graph. The cleansing level bar further includes a horizontal dashed line 322, which may represent a threshold level that may assist the user in evaluating whether the cleansing level at any given point is above or beneath that threshold value. The threshold value may be, for example, the average value or a limit for the proper values.

The map shown in FIG. 3 may be displayed in a screen separate from the screen or display of the level one images (as shown in FIG. 2) or together with the selected images.

In one embodiment, images from the series of captured images may be automatically selected. A map including indications of the automatically selected images is initially displayed to the user or by default (e.g., a pre-populated map). The map includes markings of automatically identified regions or segments of the imaged organ. The user can then access a more detailed presentation of regions of the map that he or she may wish to explore.

In one embodiment, the user is presented with a graphical representation (e.g. a map) of the entire case, e.g., the entire portion of interest of the GIT (e.g. the entire SB or the entire colon). For example, the user may be presented with a graphical representation of the entire spread of the small bowel, divided into three tertiles, e.g., based on an automatic identification of the entry of the capsule endoscope into the small bowel, its exit from the small bowel, and a measurement of the passage time in between. In some embodiments, the division of a GIT portion may be based on an estimation of the length traversed by the capsule endoscopy device. Markings on such a graphical representation (e.g., in the form of full vertical lines) may indicate automatically selected images, e.g. level one images or images of the selected subset of images, that may be or are likely to be images of interest. Diffusive findings (e.g., regions of the organ that may include groupings of images of interest or multiple images of interest in proximity) may be identified on the map. In such an embodiment, diffusive findings may be displayed as bars having a lighter shade than the image of interest markings and extending from the respective location of the beginning of the image grouping to the respective location of its end.

Figure 4:
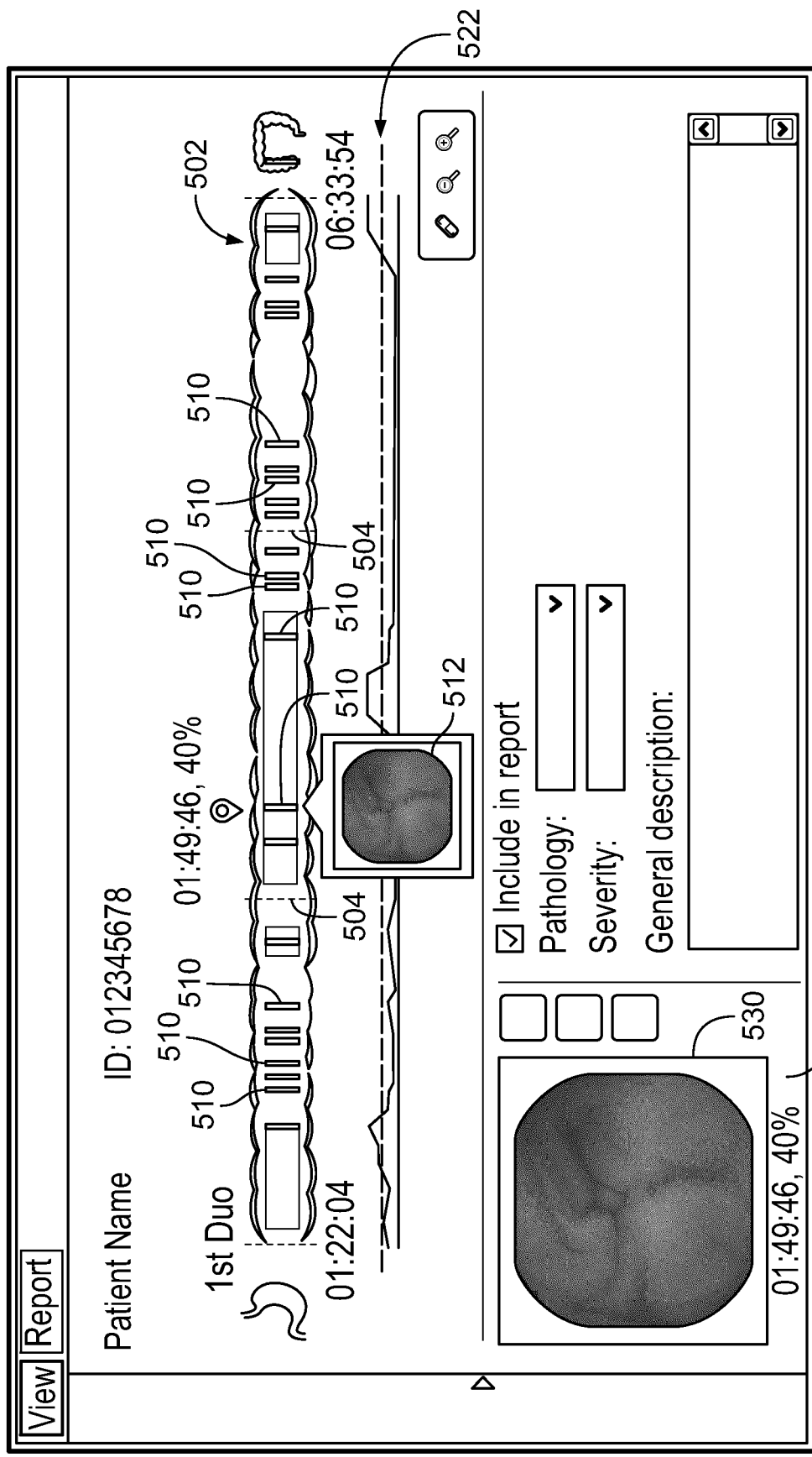
FIG. 4 shows an example screen or display with additional information, e.g. a study, displayed, according to some embodiments.

FIG. 4 shows an example screen or display with additional information displayed. In the same screen, the user may view the selected images, e.g., by providing input by clicking on or hovering over the respective markings 510 on the map 502. When the user selects an image, e.g., by clicking on the respective marking 510 or thumbnail 512 that is displayed in the map's display area, a larger version 530 of the same image may be displayed in the "additional information" area 540 (e.g., here, in the lower left corner of the screen). The user may then view additional images from the respective segment of the organ or a short clip including images captured before or after the selected image (e.g., images surrounding the selected image). Other functionality may be available to the user, such as the addition of notes or markings to the displayed image or the selection of the image for inclusion in a report. The markings 504 of the division of the organ into segments (e.g., the tertile division marking) may be displayed in their respective locations on the graphical representation of the section.

Figure 5:
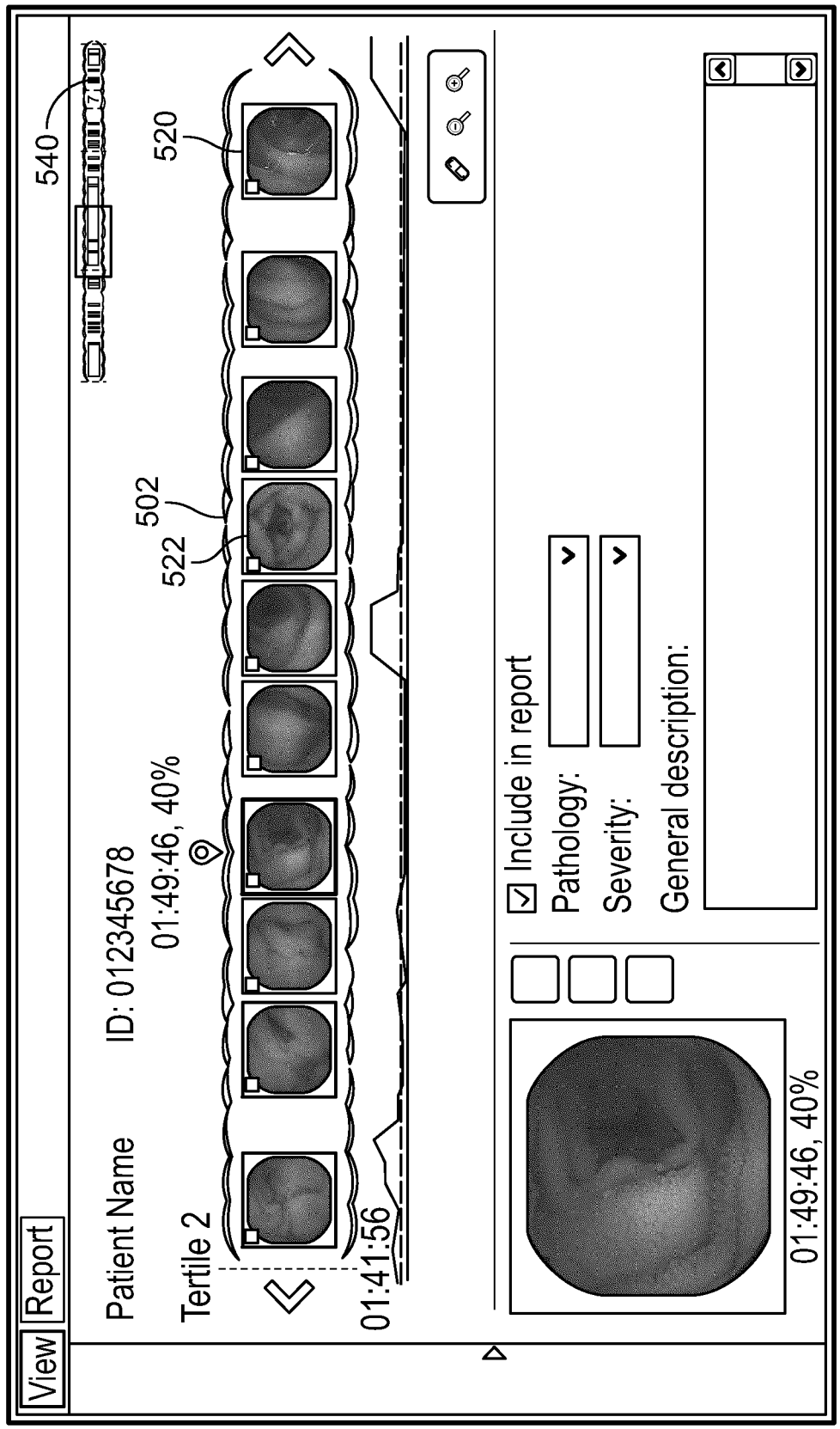
FIG. 5 shows the example screen of FIG. 4 following a zoom-in operation, according to some embodiments.

FIG. 5 shows the example screen of FIG. 5 following a zoom-in operation. In some embodiments, the user may input a "zoom" in command, to cause a system, e.g. workstation, to zoom-in on a region or section of the entire map 502, to view groups of selected images from that respective section. The selected images of (e.g. corresponding to) the respective section may be displayed, for example, as a series, grid, list ordered by time 520, etc. of thumbnails 522 on a graphical representation of the respective region. The user may also navigate (e.g. by providing input to a GUI)

between sections or sub-regions of the map using a reduced representation of the map 540, as shown in the example of FIG. 5, for example, in the upper-right corner of the screen.

In some embodiments, the user may edit the map, e.g., by providing input via a GUI to cause a process to remove markings of selected images, e.g., if the user determines the respective image is not an image of interest.

After completing the review, the user may cause a process to proceed to display a report generation screen, wherein the user may review the images selected for the report, e.g., images selected by the user, as images of interest.

In one embodiment in a default view mode the images selected automatically may be displayed in a still manner and in a column layout in one side of the screen, e.g. a vertical column on the right side of the screen. The user may select an image to be displayed in an image display area, e.g. on the left side of the screen. Each selected image may be displayed with an indication of the identified area of interest within the image, e.g., by coloring the area of interest in a specific color. The display may include check boxes which refer to the identification of the area of interest. The user may then identify the area of interest and check the appropriate check box accordingly (e.g., bleeding, ulcer or other). A map or a heat map of the entire portion of interest of the GIT or a section of it may be also displayed, for example, beneath the image display area. The map may include indications of the selected images and may be used by the user to navigate between these images as well.

In one exemplary embodiment, the review of the images may be performed based on two levels of information. The first level of information may be presented in a default view mode and the second level of information may be displayed upon a user's request (e.g. user input to a GUI received to a process executed by a system such as shown in FIG. 1) or following a user's action. The default view mode may include a display of images automatically selected (e.g. by a system such as shown in FIG. 1) from the series of images captured in the GIT or a portion of it (e.g., the small bowel). The imaged portion of the GIT is divided into a plurality of segments (e.g., the SB divided into three segments/tertiles or the colon divided into five anatomical portions or segments). The selected images are displayed in a still manner and according to the segments they are located in. The user may browse the still images. The default view mode also may include a display of a map of the entire imaged GIT portion indicating the segments and the selected images according to their estimated location within the segments. In some embodiments, the default display of the map may include only the segment/s in which the displayed images are located. In some embodiments, the user may provide input to a process to cause a zoom in (e.g. expansion of the size of images displayed) to a section of the map representing a section of the imaged GIT portion.

The second level of information may include the display of additional images surrounding the selected images and may be displayed separately (e.g., in a pop-up window or screen) from the first level images. The default view or display (e.g., the first level of information) may also include indication of the sections of the imaged GIT portion which are displayed in the second level of information. The default view may further include indication of the level of cleansing of the series of images captured in the GIT portion. The surrounding images displayed in the second level of information may be displayed in a still manner and/or as a video clip, short movie or moving image.

Figure 6A:
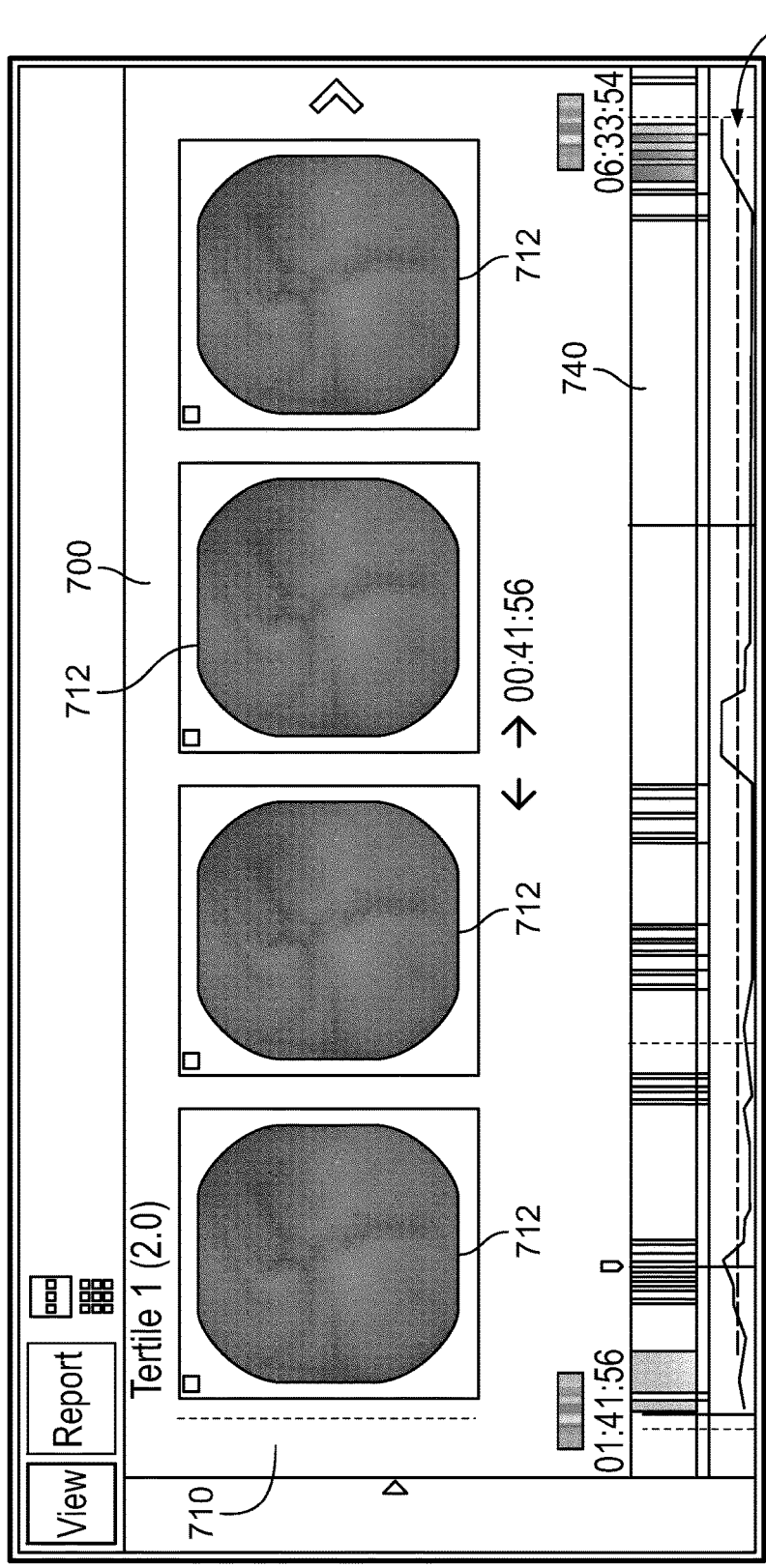
FIG. 6A shows a schematic illustration of a study view mode according to an embodiment of the invention.
Figure 6B:
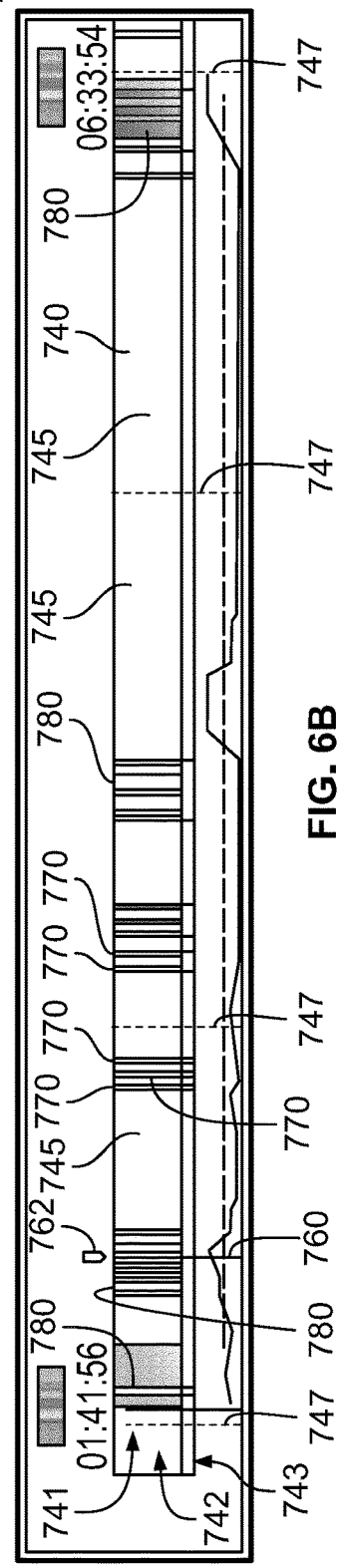
FIG. 6B is a schematic illustration of the map (e.g. a bar) in the default view mode of FIG. 6A, according to one embodiment.

FIGS. 6A and 6B provide examples of cases displayed and analyzed of the small bowel.

FIG. 6A shows a schematic illustration of a default view mode according to disclosed embodiments. FIG. 6B is a schematic illustration of the map (e.g. a bar) in the default view mode of FIG. 6A, according to one embodiment.

According to an embodiment shown in FIGS. 6A and 6B, a default view 700 may include a simultaneous display of a set of still images 712, which includes only a few images (e.g., four images), thus allowing the user to carefully and clearly review the displayed images. The set of images may be displayed in a row 710 layout, thus simulating the layout of the GIT, or another layout. The images may be displayed substantially in the center of the view. The user may move the focus (e.g. the primary or largest display) between the images in the displayed set of images or scroll between the sets of images, e.g. via user input. The selected images in each segment (e.g. each tertile) may be divided into such sets of images and displayed according to their chronological order (e.g., according to their capture time). The tertile which the currently displayed set of images belongs to may be indicated in the view.

The default view may include a map 740 located for example in the bottom of the screen, as the example shown in FIGS. 6A and 6B. Map 740 may be in the form of a bar or a row or line format and may include sub-rows (e.g. three rows) representing types of information, in one example three types of information indicated 741, 742 and 743 in FIG. 6B. The example map is of the entire small bowel. The map may be divided into sections such as the three tertiles 745 by broken vertical lines 747. The map may also include a portion of the colon. An image in-focus may be indicated in the map by a vertical line 760 colored differently and/or a cursor 762, as shown in FIGS. 6A and 6B (e.g. by a blue line 760 and cursor 762). The frame of an image in-focus may be also colored differently (e.g., in blue, as shown in FIGS. 6A and 6B). The user may also receive an indication whether a frame was already reviewed in the second level of information. Thus, for example, the frame of an image which was already reviewed in the second level may also change its color, e.g., from black to grey.

The first sub-row 741 in FIG. 6B includes a heat map indicating the selected images located along the imaged GIT portion, here including the small bowel. The selected images are indicated as vertical lines 770 of a specific color (e.g., grey) and are located along the bar according to their estimated location along the small bowel. The user may provide input (e.g. a mouse hover over) to a line representing an image to receive a display of a thumbnail of the image (e.g., a reduced image) with an indication of its capture time. Portions of the bar may be colored in different colors to indicate anatomical areas of interest, as shown, for example, in FIGS. 6A and 6B (e.g. provided as light blue areas indicating an estimation of the proximal and distal area of the small bowel). At the end of the heat map, at least one image of the next anatomical portion of the GIT, here the colon, may be displayed, inter alia, to exhibit that the entire small bowel or the GIT portion of interest was imaged and that the procedure was completed. The line indications of the mages may change their color once they were reviewed by the user (e.g., to orange).

The second sub-row 742, may include indications to the sections of the imaged GIT portion, here, the small bowel, which their images will be displayed in the second level of information. These sections may be indicated by indications 780 such as grey-colored rectangles. Each rectangle, e.g., a second-level section, may include and/or relate to one or more selected images of the first level, as one may see in FIGS. 6A and 6B. This is in case two or more first level selected images are relatively proximate to each other.

The third sub-row 743 may include a graph indicating the cleansing level of the captured images along, e.g., the small bowel. The graph may be colored according to the level value, e.g., it may be colored in red when the value (e.g., cleansing) is relatively low.

The passage between different anatomical sections of the imaged GIT portion, e.g., Gastro-to-SB (e.g., stomach to Small Bowel) and/or SB-to-Colon, may be also indicated, as shown in FIGS. 6A and 6B. The passage may be indicated above the relevant segments' indications in the map (e.g., the broken lines), and may include the passage time. Optionally, a small color bar may be displayed above the relevant segments' indications, representing a series of images captured in the identified passage area. The user may provide input (e.g. hover) to the color bar and review the passage images. The color bar may represent only a sample of the images of the identified passage area.

Images as shown in FIG. 6A may differ; for example selected images may be displayed in a matrix form and thus more images may be displayed simultaneously. A user may request, for example, to use other display modes of view instead of the mode of view of FIG. 6A. According to such an alternate view, the images of each tertile may be displayed in a separate matrix, e.g., in a separate tab. The user may scroll between the images in each tertile.

Figure 7:
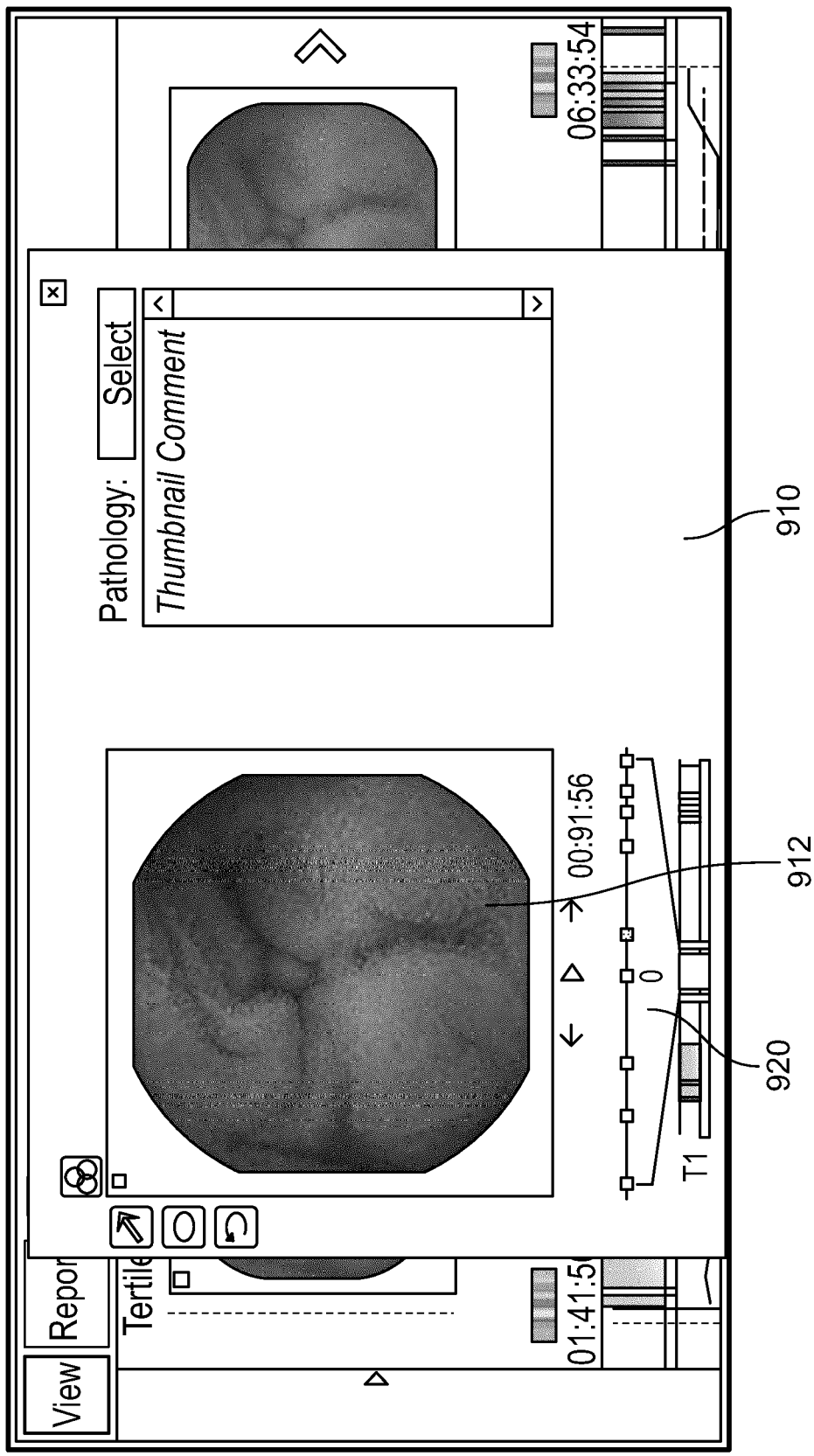
FIG. 7 shows an example illustration of a display or view of a second level of information of an image selected according to the display illustrated in FIG. 6A, according to some embodiments.

FIG. 7 shows an example illustration of a display or view of a second level (e.g. study) of information of an image selected according to the display illustrated in FIG. 6A.

The second level of information may be realized according to the present embodiment by a pop-up window 910 which displays the selected image 912 by default. The window/display/view may display a sub-series of images which surround (e.g. are several images before and after, or were captured several seconds before and after) the selected image. The user may use an input device such as a mouse scroll wheel to cause a process to scroll (e.g. move forwards and backwards in sequence or time) the images in a still manner or he may cause a process to display the sub-series of images as a video clip. A map 920 may be displayed beneath the images display area.

According to the example in FIG. 7, the map may include a portion of the first sub-row of the map of the default view in the first level, which represents the relevant segment of the imaged GIT portion. The section which represents the sub-series of images of the second level may be indicated in color, for example orange. An additional second level map may be presented above the portion of the first level map, which includes indication of the selected images of the first level display that are included in the second level sub-series of images. When such an image, e.g., a first level selected image, is displayed in the image display area of this second level data pop-up window, it is indicated in this second-level map (e.g., by squares; in the example shown, the relevant square is colored in blue and a blue cursor is located above that mark).

A portion of the first level map, which represents the section which includes the second level images, may be displayed below the images display area. The selected images are indicated in this map and the first level selected image which is in review is indicated, e.g., by coloring the image line indication in a different color.

In one embodiment, one image at a time may be selected from a group or "pile" of selected images by browsing the mages horizontally (e.g., in a carousel manner). A heat map representing the imaged GIT portion and indicating the selected images may be displayed, e.g., above the image display area. Each image displayed may be referred to its indication in the heat map, e.g., by a line connecting the image and its point or representation on the heat map or map.

One embodiment may display one image at a time from a group or pile of selected images. The user may view a single image by using an input control (e.g. a mouse, a scroll wheel, etc.) to provide input to a GUI to cause scrolling through the mages vertically to select one image at a time. A heat map or other map representing the imaged GIT portion and indicating the selected images may be displayed, e.g., next to the image display area. Each image displayed may be referred to its indication in the heat map, for example by a connecting line linking the image to the relevant heat map or map position or image indication.

A default view mode, e.g., a main view of a default view of a study, may include a display of a heat map representing the imaged GIT portion and indicating selected images. The images may be located in the heat map according to their estimated location in the imaged GIT portion. A selected image may be displayed in an image display area. The selected image may be displayed in a still manner or as part of a video clip including additional related images per the user's request or following a user's action. The user may hover or click, for example, on an image indication on the heat map, to receive, for example, a thumbnail of the image and/or a still display and/or a clip.

Figure 8A:
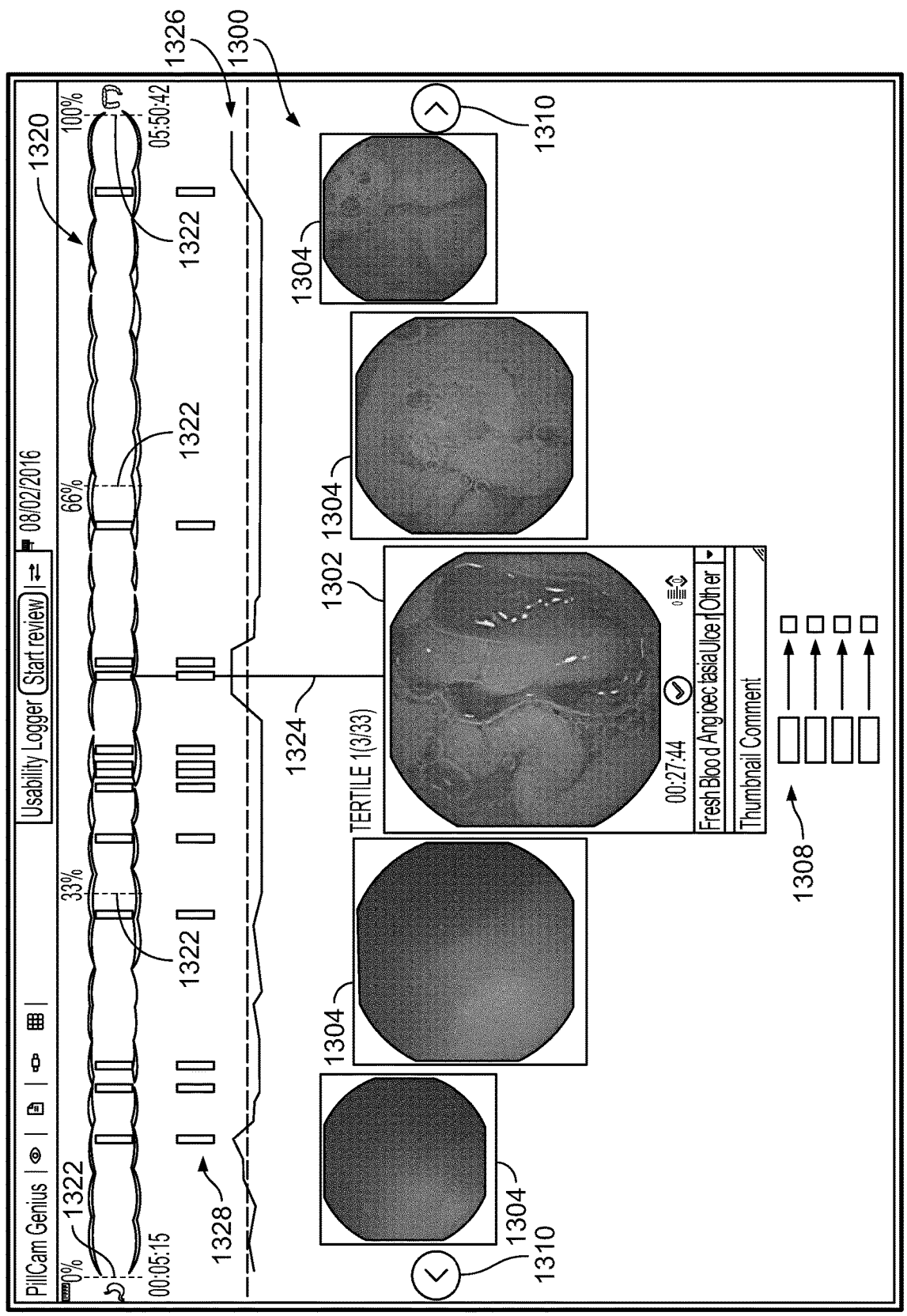
FIG. 8A depicts a default study view according to an embodiment.

FIG. 8A depicts a screenshot or display of an optional view mode according to an embodiment. In an embodiment shown in FIG. 8A, first level or images of the selected subset of images may be displayed in a slider manner or "carousel manner" 1300 and such that one image 1302 is displayed more prominently at a center, with other images 1304 to the side in decreasing size with distance from the main center image 1302, such that user input (e.g. to arrows 1310 at the edge of the screen, or using a mouse scroll bar), causes "rotation" such that another image of other images 1304 in the view is moved to the center to become the center image 1302. A map 1320 with cleansing 1326 and other additional information may be displayed (typically above) the first level image carousel display 1300.

Second level images may be displayed in the same window of first level and thus there may be no need to activate another window. The user may, for example, hover on the image or click it and then the image is "activated" or becomes "in-focus" as shown in FIG. 8A. For example, a user may provide input to a GUI to switch to level two, and the center image 1302 may be viewed as a video or image stream, or a "scrollable" sequence of images displayed in a still manner, of all the images related to or associated with the specific instance (e.g., second level images) represented by the one center image in level one.

In this embodiment, still images (e.g., automatically pre-selected images) are displayed horizontally in carousel form 1300. In the specific example in FIG. 8A five images are displayed simultaneously. The central image 1302 is the image which is in focus. Following that, the number of images typically displayed simultaneously is typically an odd number of images. In some embodiments, various odd-numbers of images may be displayed simultaneously. The images may be displayed in a carousel manner, allowing the user to horizontally browse among the images and such that no image conceals the other. The size of the images changes according to their position in the display carousel 1300. The central image 1302, which is the in-focus image is the largest. The size of the other images 1304 changes with respect to their closeness to the central image. The closer the image to central image 1302, the larger it is. Such a layout may allow a user to closely and more clearly review one image and at the same time review and receive information with respect to adjacent or surrounding images. Such view may allow comparison between adjacent images while still displaying the image in-focus in detail.

Bar or a map 1320 (e.g., a heat map) may depict a representation of the entire imaged GIT portion or of a section of it. The exemplary display displayed in FIG. 8A is of the small bowel. The map 1320 is displayed above the display of the images and on the top area of the screen. Accordingly, the map represents the small bowel and is divided into three tertiles (e.g., by broken vertical lines 1322). The map may include information with respect to the location of the displayed images along the imaged GIT portion and/or of the cleansing level of the displayed images and/or the captured images and/or the imaged GIT portion. The map may include two or more sub-rows presenting the different information. The image in-focus may be indicated in the map, for example, by a connecting line 1324, as shown in FIG. 8A. In some embodiments, all the currently displayed images may be indicated in the map (e.g. by symbols or lines, or connecting lines).

In the present embodiments, the map 1320 includes two sub-rows 1326 and 1328. The first sub-row 1326 may include information with respect to the cleansing level of the captured images. In the present embodiment, the cleansing level is presented in the form of a graph and may be presented in the form of a color bar (as in FIG. 10). Different colors indicate different cleansing level categories, such as: low, medium and high. The second sub-row 1328 may include a bar on which the selected images are indicated (e.g., by vertical lines) and according to their estimated location along the imaged portion of the GIT.

Furthermore, according to the present embodiment, the second level of information is presented in the same initial or default screen (e.g., a main or default screen of a study view). The image in-focus (e.g., the central image 1302) is shown with additional controls 1308 which allow the user, for example, to scroll between images surrounding the selected image as a second level display. The scroll bar may indicate a numbering of the surrounding images with respect to the image in-focus. For example, the image in-focus may be indicated as "0", the next image to the right "1", the next one to the right "2" and so on. The image previous to the image in-focus (i.e., the next image to the left) may be indicated "4", the one before that "−2" and so on. Thus, the user may be oriented with respect to the distance and direction (in images and time) relative to the original selected image 1302. Furthermore, text boxes may be displayed beneath the image in-focus which allow the user to input information such as the identified type of pathology and comments. In some embodiments, the second level controls and/or data may appear (e.g., beneath the image) once the image is selected as the image in focus and/or once the user places the image as the central image 1302 (e.g., by scrolling) or once the user hovers over the image in-focus, click it or upon any other user action.

Figure 8B:
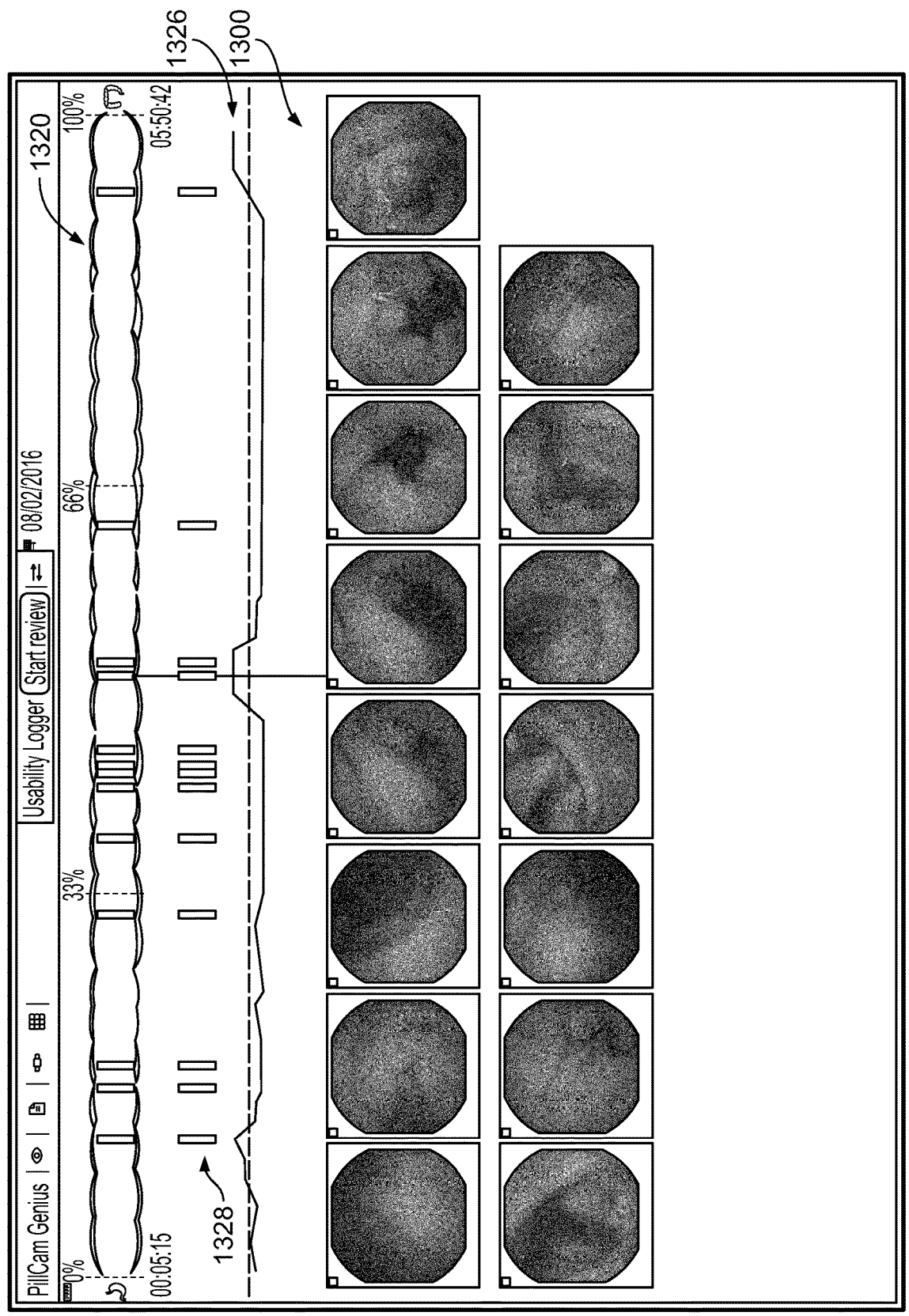
FIG. 8B depicts a matrix layout of images shown in FIG. 8A, according to some embodiments

FIG. 8B depicts a matrix layout of images 1300 shown in FIG. 8A.

Figure 9A:
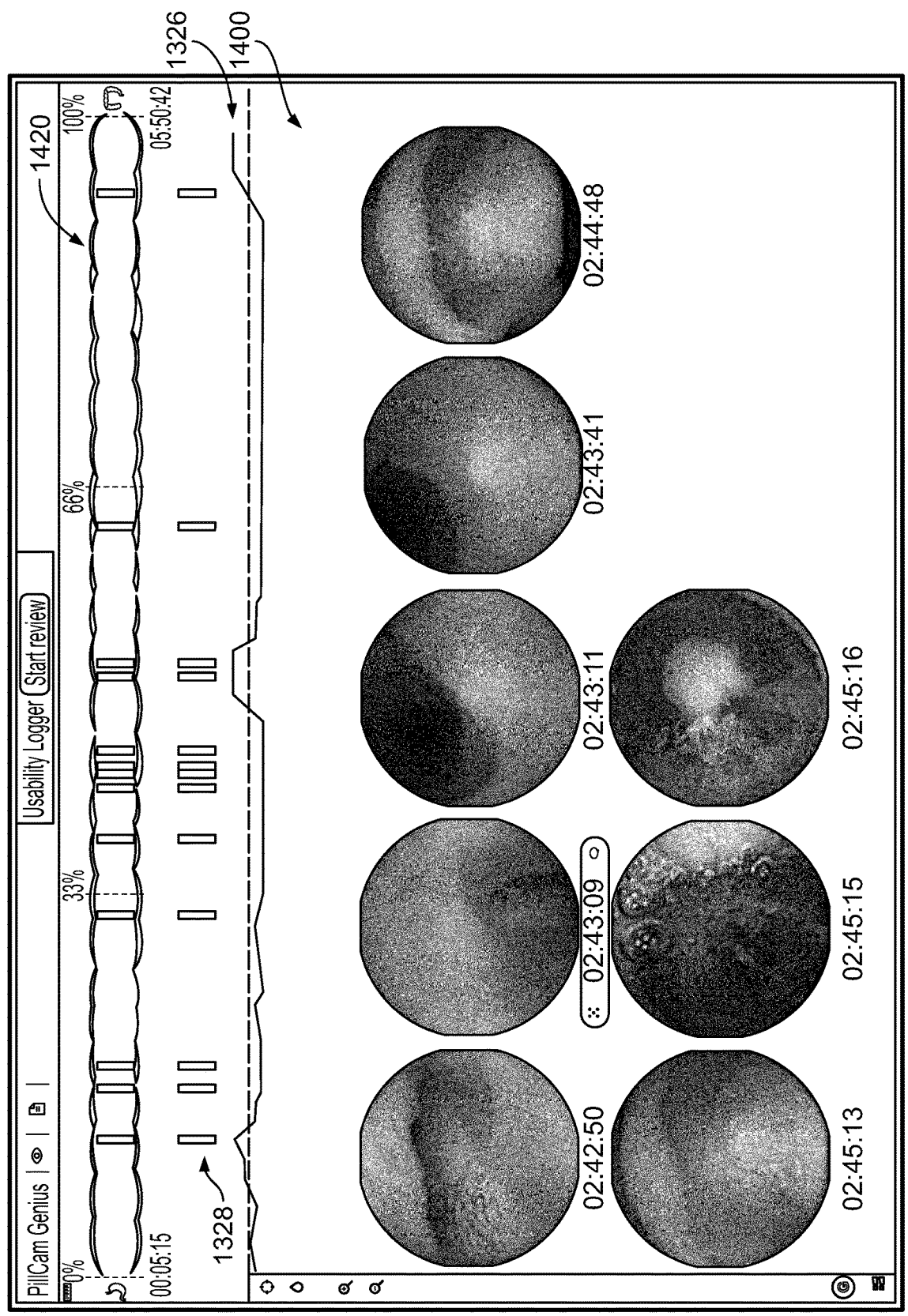
FIG. 9A is an example screen shot of a default view mode according to an embodiment of the present disclosure.
Figure 9B:
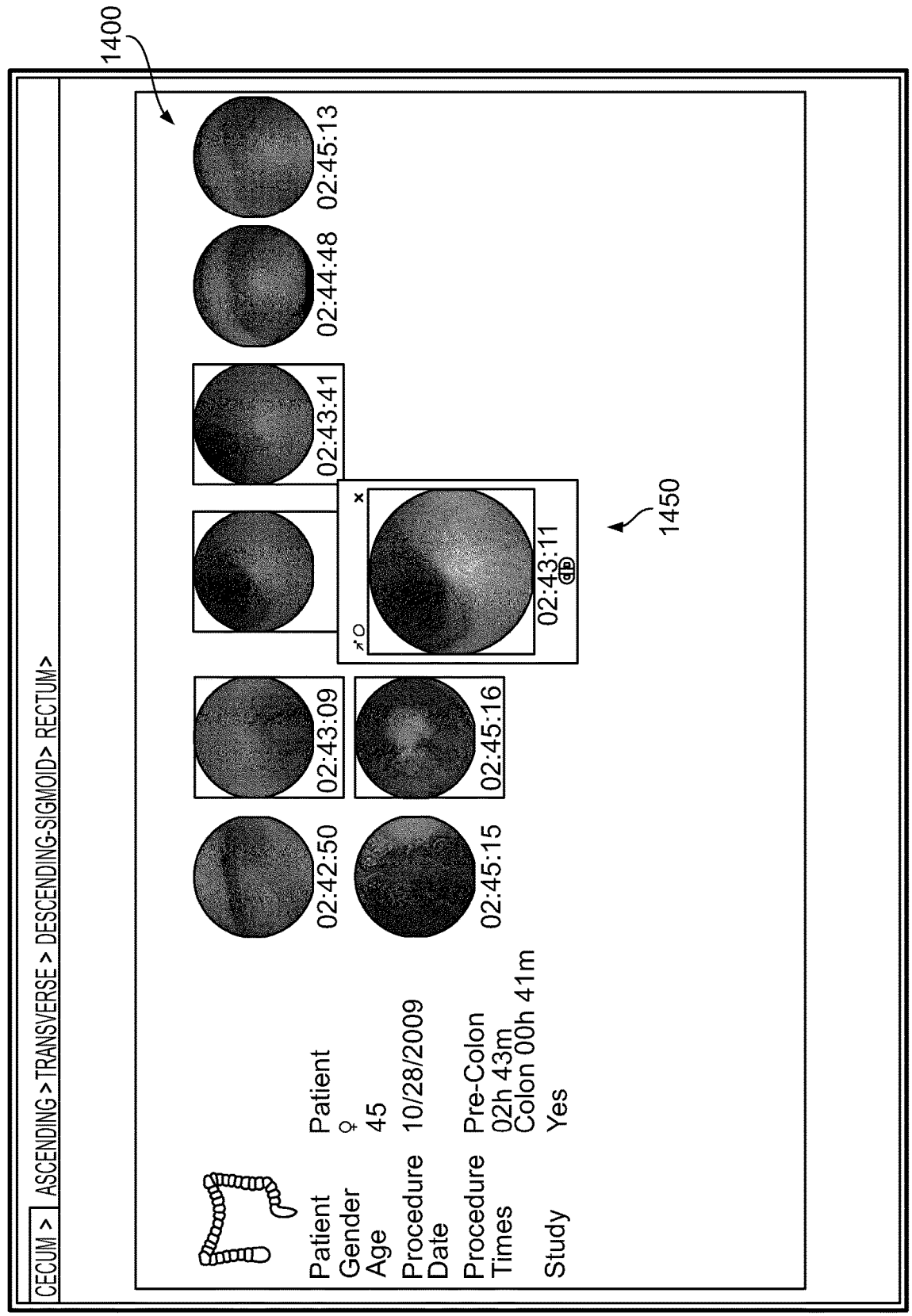
FIG. 9B is an example screen shot of a display or view of a second level of information of an image selected in the display of FIG. 9A.

FIG. 9A is an example screen of a default view mode according to an embodiment of the present disclosure. FIG. 9B is an example screen shot of a display or view of a second level of information of an image selected in the display of 9A.

In this embodiment, the case displayed for review is of the colon. In the default screen (e.g., a default screen of a study view), as shown in FIG. 9A, images selected (e.g. automatically, by an image selection process) from the stream of images captured during the procedure are displayed in a matrix 1400 form. The colon may be divided into five anatomical segments: cecum, ascending, transverse, descending-sigmoid and rectum. The selected images displayed may be localized (e.g. displayed with localization information) according to the five segments and displayed per segment—e.g. an image may be localized not with a specific location, but rather by being indicated as being within one of the five colon segments, or in another GIT segment or category. The images of each segment may be displayed in a dedicated display area and the user may switch between the displays of the segments by tabs. The specific screen shown in FIG. 9A shows images identified as being captured in the descending-sigmoid segment. Images selected by the user as images to be included in a report may be indicated by for example blue-colored frames 1410. Additional information 1420 may be displayed to the user. Such additional information may be (FIG. 9B): an illustration of the colon indicating which segment is displayed, patient relevant details, date of procedure, the procedure time in the relevant regions of the GIT (here the pre-colon region and the colon), and if the study was complete (in the example shown, if the capsule reached the end of the colon). Such procedure times and completeness indication may be determined based on identification of relevant landmarks, such as: passage or entrance to the colon and body exit.

Further information, e.g., the second level of information, may be displayed upon the user's request. For example, a user may click on a displayed image to open a pop-up window 1450 which displays the image by default and allows the review of additional information, as shown in FIG. 9B. The additional information displayed or may be displayed (e.g., upon the user's request) according to the present embodiment may include an automatic indication of an area of interest in the image, e.g., of a polyp or by which head of the capsule the image was captured, in case the capsule endoscopy includes more than one camera. The indication of the area of interest may be, for example, by segmenting the area, and/or by an arrow pointing to such an area. Automatic identification and indication of the area of interest (e.g., a suspected polyp) may provide guidance to the physician and improve the diagnosis, e.g., detection of polyps.

Figure 10:
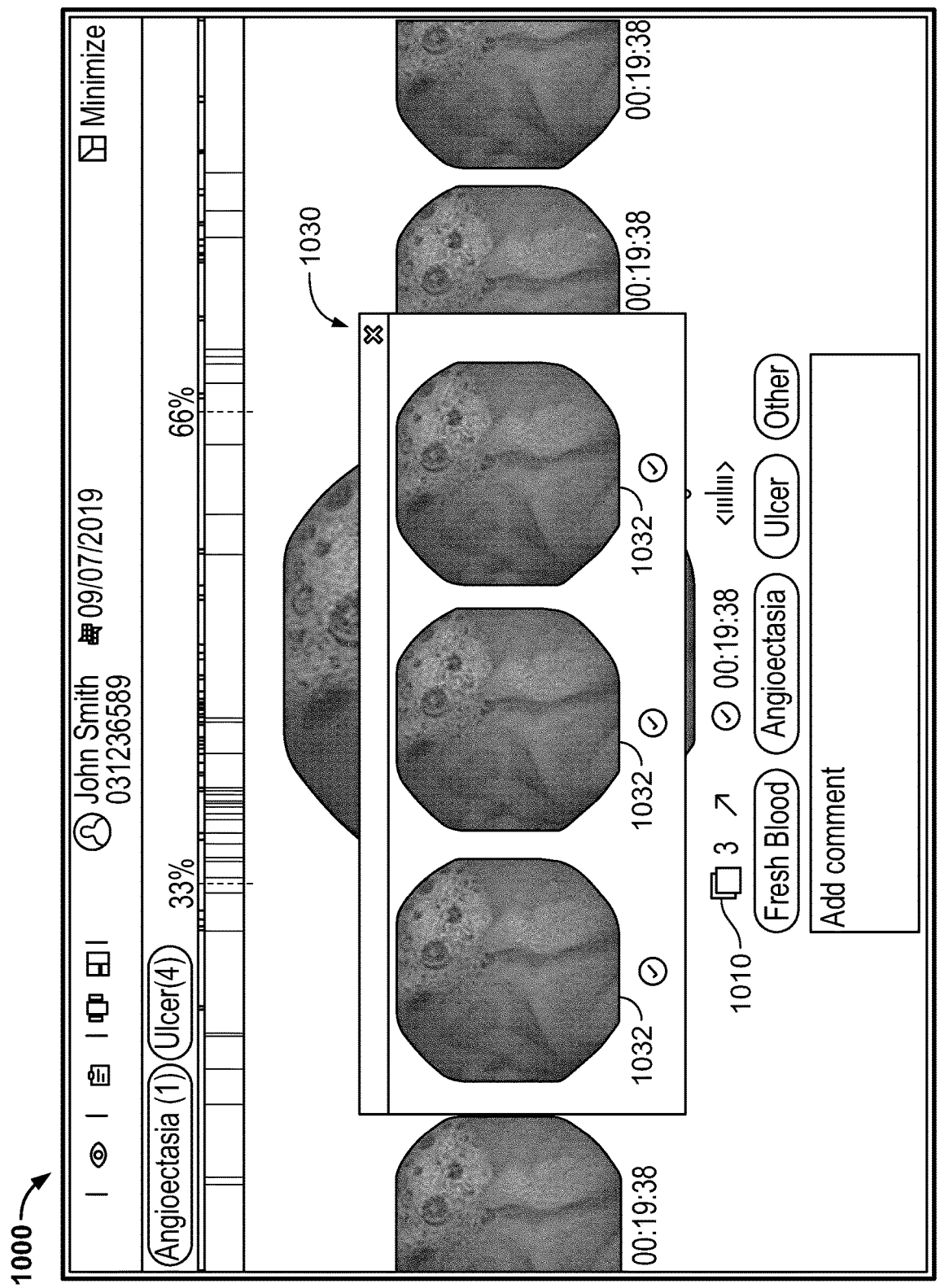
FIG. 10 depicts a sample display according to an embodiment of the present invention.

FIG. 10 depicts a sample display according to an icon 1010 (in one embodiment a depiction of a pile of images with the number "3" near it corresponding to the three images 1032 which are selected by the user). Selected images 1032 may be included within a window or dialogue box 1030. A user may click or select (e.g. using a mouse to input to a GUI) on icon 1010, a system may cause window 1030 to appear including user-checked or selected images. The user may then review the checked images 1032 all at once in an adjacent or row manner.

In another embodiment a system may display a certain number of the most relevant or suspected images (e.g. "top X most suspected images", e.g. 5 or 10 most relevant images) in another view or display. Such view may provide a first quick indication for the user, and may be beneficial for colon screening, for example. In a colon screening context a user may want to determine if there is a polyp or not (a polyp may indicate the potential for cancer and the need for a colonoscopy). The view may be added in another tab or window.

An automatic polyp (or other feature) size estimation function may, in response to a user's request, calculate and provide an indication of a polyp's diameter, length or other size estimate. The size of a polyp or feature may be automatically calculated by for example measuring the greatest distance between two points in the identified polyp perimeter. The user may select other points for measuring the polyp's size and a process may calculate the size according to the user's selection. For example, the display of the feature or polyp may include a bounding box for the polyp, such that the polyp is located within this box. A line in the bounding box may be displayed, representing the length measured, and the size may be displayed or presented, e.g. near that line. The user may change the location of each of the two ending points of the line in case the user believes that the automatically selected points are not accurate. One advantage of automatic polyp size estimation, or of any other feature of interest, is standardization. For example, current methods determine polyp size based on manual user input (e.g., the points defining a length of the polyp) or according to a manual estimation, and different users or different user's input may provide or lead to different size estimations for the same polyp.

In some embodiments a cleansing level or other data may be displayed per image, per segment, and/or per procedure.

In some embodiments an option may be provided to present in each segment, the most suspected images first (e.g. in matrix view), or by another method, e.g., by asterisk.

In some embodiments, a representation of the GIT portion of interest in a map may indicate also second level images, not just first level images. Thus, for example, the extent of diseases and pathologies may be also represented.

In some embodiments, to provide a personalization of a study, the parameters of the study (e.g., how many images would be included in first/second level, how many images of the study would be selected to represent a certain segment of the studied GIT portion, thresholds for selecting an image to be included in the study etc.) may be adjusted or determined per patient. In some embodiments, such adjustment may be performed manually, e.g. by a user performing the procedure or the referring physician entering data. In some embodiments, such parameter selection may be automatic, or at least a portion of it (e.g., automatic adjusting for some of the parameters to be determined), e.g. based on the patient's information or details, including patient's medical history. In automatic adjusting, natural language processing (NLP) algorithms or Machine Learning-based tools may be utilized, such as the Comprehend Medical system provided by Amazon. Such tools may make free text interoperable and searchable. A system may then use the medical background of the patient to adjust the study. For example, if a system recognizes in the free text, for a patient (e.g. a case) that the patient has a family history of polyps, the system may modify the study or presentation to have more images (e.g., to increase the sensitivity of the study) as opposed to a healthy patient with no medical history of polyps.

In some embodiments speech-to-text or automatic speech recognition systems (e.g. "Transcribe" by Amazon) may be integrated to, for example, reduce reporting time significantly for free text by allowing a user to start "writing" the report using speech-to-text while reviewing the images. The use of speech-to-text may reduce the need for clicks or other manual user input. For example, a user may speak and have action taken based on "show me a picture of an ulcer from atlas"; allowing this action to be taken by the system without clicking or user manual input (e.g. to display an atlas of typical disease images that can be searched by key descriptors and used as a viewing aid for comparing study images with reference images). Speech-to-text may allow a "chat-bot" to aid a system GUI, such that a user may ask a system questions and have a system find if there is a similar enough question in a "FAQ" or other repository, and provide an answer.

In some embodiments a system may display transition sections in the GIT portion of interest. For example, instead of a color bar, an image representing the transition section from each side (e.g. stomach and colon for SB) may be presented or available, e.g., at the first level or default view of a study (and indicated in the map), having a second level display which includes the transition (between section) images. In some embodiments, the transition images (e.g. images indicating a transition between GI sections) may be displayed after user input, e.g. after the user clicks an icon indicating stomach or colon, at each end of a displayed map, accordingly. Such an anatomical transition images may include a number of images identified to be located adjacent to an anatomical transition (e.g., from SB to colon). One option for the display of transition images may be including one image for each transition in the subset of images (e.g., first level images) and then the plurality of images representing the transition as the one or more corresponding images (e.g., the second level images). The images of the subset of images may then appear in the map outside of the portion of interest (e.g. in both ends). Another option is to represent such images in a small color bar above a map at both ends of the portion of interest or, by having a user click the icons at the end of the portion (e.g. SB icon and toilet icon in a colon study) to receive a window or a screen including a display of the images.

In some embodiments, a default view of a study may show a matrix display of the subset of images, to allow a user to first quickly review first level images. Then a user may switch to another view of the study, e.g., a "carousel display" as described elsewhere. For example, clicking an image in the matrix display would initiate the display of the other study view including the carousel display of the subset of images and where the image clicked is the center image of the carousel (e.g. a kind of zoom-in view). This may be most beneficial when the study includes relatively more images (e.g. a few hundreds of images). In some embodiments, the matrix view may also include the display of second level images and/or other additional information.

In some embodiments machine learning, artificial intelligence, or AI may be used to automatically identify, localize, and size precancerous colonic polyps, and small bowel pathologies, or other features. Embodiments may use or execute modules functioning as "detectors" for certain features or pathologies such as NLH (Nodular Lymphoid Hyperplasia), ulcer, angioectasia, erosion, blood, lesion, or inflammatory stricture.

A report may be generated after user review, based on user input during the review.

Figure 11:
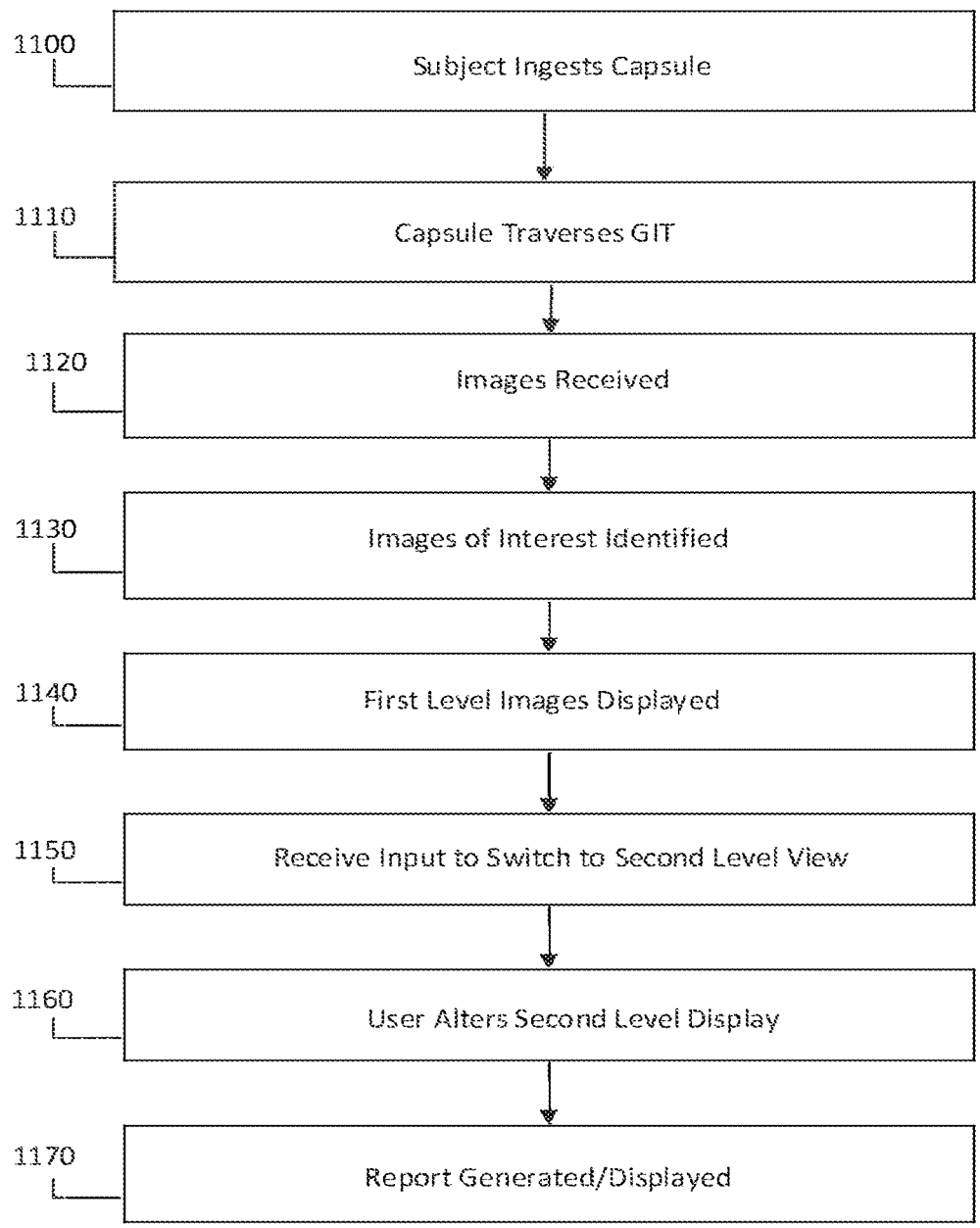
FIG. 11 is a flowchart of a method according to embodiments of the present invention.

FIG. 11 shows a flowchart of a method according to embodiments of the present invention. The operations in FIG. 11 may use a system as shown in FIG. 1, but may use other systems.

In operation 1100, a subject or patient may swallow or ingest a swallowable capsule, for example including one or more imagers or imaging devices (e.g. a digital imager or camera), a transmitter, and other units such as a power source and antenna.

In operation 1110, the capsule may traverse (e.g. by subject's natural peristalsis), the subject's GIT or a portion of the GIT, transmitting (e.g. via a radio transmitter) the images to an external receiver.

In operation 1120, the images transmitted by the capsule may be received by the external receiver (although other methods of transferring images may be used), recorded, and processed. Various combinations of equipment may be used to receive and store the images.

In operation 1130, in one embodiment, a set of images of interest may be identified or selected automatically, e.g. by one or more processors, using for example a first selection method. Each image of interest may show a different feature or pathology automatically identified. Groups of images may be created, each group including one first level image of interest and a corresponding set of images not in the first level of interest, but showing the same feature as the one corresponding first level image for that group. Each first level image may be identified as the "most representative" image in the group.

In operation 1140, the first level images may be displayed on a monitor or display device in a main or default view of the study default view (e.g. without any user input or command starting such a display) as still (e.g. non-video) images. The first level images may be a subset of images of the stream of in-vivo images. The user may review the first level images. The first level subset of images may represent the received stream of images.

In operation 1150 a user may provide and a system or GUI may receive input to display a second level images, in which on the display device or monitor one or more additional images corresponding to a currently displayed image of the subset of images may be displayed. For example, the images in the group corresponding to a selected or clicked-on first level image may be displayed. The one or more additional images in the group may have been automatically selected from the received stream of in-vivo images according to a second selection method. The second selection method may be based on a relation between images of the stream of in-vivo images and the currently displayed image.

In operation 1160, in one embodiment, a user may alter the display of the second level images; e.g. causing the images to be displayed as a moving image, or moving forward and backwards through the group of images in a still manner, e.g. using a scrolling wheel. The study may be displayed in e.g. a carousel mode, matrix mode, or another mode.

In operation 1170 a report may be generated or displayed to a user. The report may include images from the displayed images selected by the user, and possibly other information such as comments inserted by the user.

Other or different operations may be used.

Embodiments may improve the technology of capsule endoscopy procedure, and of generation of a study, medical image display, and medical diagnosis in particular, and thus may also improve the ability of a medical professional to diagnose information and to provide better and more efficient treatment. For example, medical image processing and display technology may be improved by providing systems allowing a doctor to more quickly find, view and analyze regions of interest in a GIT, and which provide automatic analysis which may support and better the doctors decisions when compared with prior medical technology. For example, in prior GIT imaging systems, a doctor may have been forced to view a lengthy video. In addition, no automatic identification, localization and/or sizing of features of interest is provided.

While several embodiments of the disclosure have been shown in the drawings above, it is not intended that the disclosure be limited thereto, as it is intended that the disclosure be as broad in scope as the art will allow and that the specification be read likewise. Therefore, the above description should not be construed as limiting, but merely as exemplifications of particular embodiments.

It should be clear that most principles, elements and features described above with respect to embodiments according to the disclosure and/or shown in the figures, are not restricted to the embodiments in connection with which they are described/shown, and may independently be applied, mutatis mutandis, to each other or to any other embodiments according to the present disclosure, in any combination considered to be appropriate by a person skilled in the art.

The invention claimed is:

1. A method for displaying a study of a capsule endoscopy procedure for a user's review, wherein the capsule endoscopy procedure comprises capturing a stream of in vivo images of at least a portion of interest of a subject's gastrointestinal tract (GIT), the method comprising using one or more hardware processors for:

displaying on a display device a subset of images of the stream of in vivo images for the user's review, wherein the subset of images represents the captured stream of in vivo images, and wherein the subset of images is automatically selected from the stream of in vivo images according to a first selection method;

in response to receiving user input selecting a currently displayed image of the subset of images, displaying on the display device one or more additional images corresponding to the currently displayed image of the subset of images, wherein the one or more additional images are automatically selected from the stream of in vivo images according to a second selection method, and wherein the second selection method is based on a relation between images of the stream of in vivo images and the currently displayed image, wherein the relation on which the second selection method is based comprises images which are identified to include at least a portion of a same feature; and generating a report, the report comprising images from the displayed images selected by the user.

2. The method of claim 1, wherein the subset of images is displayed in a still manner in a default display of the study.

3. The method of claim 1, wherein the displaying of the subset of images comprises simultaneously displaying multiple images of the subset, wherein the multiple images were captured by a single imaging device of a capsule device used in the capsule endoscopy procedure.

4. The method of claim 3, wherein the simultaneously displayed multiple images of the subset are displayed in a layout of a carousel or a matrix.

5. The method of claim 1, wherein the relation on which the second selection method is based is further selected from the group consisting of: images which are identified to include at least a portion of a same type of feature, images which were captured in time proximity, images which are localized adjacently along the at least portion of interest of the subject's GIT, and combinations thereof.

6. The method of claim 1, further comprising using the one or more hardware processor for:

selecting the subset of images according to the first selection method; and for each image of at least a portion of the subset of images, selecting the one or more corresponding additional images from the stream of in vivo images according to the second selection method.

7. The method of claim 1, wherein the one or more additional images comprises at least one image of the stream of images which is not included in the selected subset of images.

8. The method of claim 1, wherein the one or more additional images comprises only images of the stream of images which are not included in the selected subset of images.

9. The method of claim 1, wherein the one or more additional images are displayed simultaneously with at least a portion of the currently displayed image on the display device.

10. The method of claim 1, further comprising using the one or more hardware processors for displaying a map representing at least the portion of interest of the subject's GIT and corresponding at least to the selected subset of images, wherein the map includes localized image indications representing the images in the subset of images according to their estimated location along the at least portion of interest of the subject's GIT.

11. The method of claim 1, wherein the subset of images is displayed in a matrix layout in a default display of the study.

12. The method of claim 1, wherein at least the first selection method is based on deep learning techniques.

13. The method of claim 1, further comprising using the one or more hardware processors for displaying an indication of a location in a displayed image suspected to include at least a portion of a feature of interest.

14. The method of claim 1, wherein:
the at least portion of interest of the subject's GIT is divided into segments; and
images of the subset of images are localized along at least the portion of interest of the subject's GIT according to the segments, and
the method further comprises using the one or more hardware processors for displaying an indication to the segments in which the currently displayed images of the subset of images are located.

15. The method of claim 14, further comprising using the one or more hardware processors for displaying the subset of images according to the segments.

16. The method of claim 1, further comprising using the one or more hardware processors for displaying an indication of an estimated cleansing level of images of the captured stream of images.

17. The method of claim 1, further comprising using the one or more hardware processor for:
estimating a size of a feature identified in a displayed image; and
displaying an indication of the estimated size.

18. The method of claim 1, further comprising using the one or more hardware processor for displaying, upon user input, a plurality of images selected from the stream of in vivo images representing a transition from one anatomical section to another anatomical section of the at least portion of interest of the GIT.

19. The method of claim 1, comprising displaying the study, wherein the study does not comprise any images of the captured stream of in vivo images, other than the subset of images and the additional images corresponding to images in the subset.

20. The method of claim 1, further comprising using the one or more hardware processors for filtering the display of the subset of images based on user input.

21. The method of claim 1, wherein according to the first selection method, images identified to include a feature of interest are selected.

22. The method of claim 21, wherein the feature of interest is selected from the group consisting of: a pathology, a foreign body, an anomaly, an anatomical feature and a combination thereof.

23. A method comprising using at least one hardware processor for:
receiving a subset of images automatically selected from a stream of in vivo images of at least a portion of interest of a subject's gastrointestinal tract (GIT) captured via a capsule endoscopy procedure, wherein the images of the subset of images are selected based on a first selection method;
displaying on a display device the subset of automatically selected images in a still manner;
in response to receiving user input selecting a currently displayed image of the subset of images, displaying, on the display device, additional information corresponding to the currently displayed image, wherein the additional information comprises one or more additional images automatically selected from the stream of in vivo images and according to a second selection method, wherein the one or more additional images are displayed simultaneously with at least a portion of the currently displayed image on the display device; and
generating a report, the report comprising images from the displayed images selected by the user.

24. The method of claim 23, wherein the one or more additional images are displayed in the same window as the corresponding currently displayed image.

25. A method for generating a study of a capsule endoscopy procedure for a user's review, wherein the capsule endoscopy procedure comprises capturing a stream of in vivo images of at least a portion of interest of a subject's gastrointestinal tract (GIT), the method comprising using one or more hardware processors for:
selecting a subset of images from the captured stream of in vivo images according to a first selection method, wherein the selected subset of images represents the captured stream of in vivo images;
for each image of at least a portion of the subset of images, selecting one or more corresponding additional images from the stream of in vivo images according to a second selection method, wherein the second selection method is based on a relation between images of the stream of in vivo images and the respective image, wherein the relation on which the second selection method is based comprises images which are identified to include at least a portion of a same feature; and
generating the study of the capsule endoscopy procedure, wherein the study comprises the selected subset of images and additional information, and wherein the additional information comprises the selected one or more additional images corresponding to each image of at least a portion of the subset of images.

26. The method of claim 25, further comprising using the one or more hardware processors for displaying the study on a display device for a user's review.

27. The method of claim 26, wherein the displaying of the study comprises:
displaying the selected subset of images on a display device; and
upon user input, displaying on the display device the one or more additional images corresponding to a currently displayed image of the subset of images.

28. The method of claim 25, wherein the generating of the study comprises generating additional information, in addition to the additional one or more images corresponding to images of the subset of images, selected from the group consisting of: division of at least the portion of interest of the GIT into segments, locations of images of the stream of images along at least the portion of interest of the GIT, a map representing at least the portion of interest of the GIT comprising indications of images of the subset of images along at least the portion of interest of the GIT, a plurality of images selected from the subset of images according to a third selection method, indications of features of interest in images, indication of cleansing level, indication of estimated size of a feature of interest, indication of extent of a feature of interest, a selection of images of the stream of in vivo images representing transition between anatomical sections of at least the portion of interest of the GIT, and combination thereof.

29. A system for displaying a study of a capsule endoscopy procedure for a user's review, wherein the capsule endoscopy procedure comprises capturing a stream of in vivo images of at least a portion of interest of a subject's GIT, the system comprising:
one or more processors;
a non-transitory storage device having stored thereon instructions which when executed by one or more processors cause the one or more processors to execute the methods of claim 1; and
a display device configured to display the study.

30. A system for generating a study of a capsule endoscopy procedure for a user's review, wherein the capsule endoscopy procedure comprises capturing a stream of in vivo images of at least a portion of interest of a subject's GIT, the system comprising:
one or more processors; and
a non-transitory storage device having stored thereon instructions which when executed by the one or more processors cause the one or more processors to execute the method of claim 25.

31. The system of claim 30, further configured for performing the capsule endoscopy procedure, the system further comprising a capsule device, the capsule device comprising at least one imaging device configured to capture the stream of in-vivo images while the capsule device transverses the at least portion of interest of the patient's GIT, wherein the captured stream of in vivo images is provided to the non-transitory storage device, and wherein the non-transitory storage device is further configured to receive and store the provided stream of in vivo images.

* * * * *